(12) United States Patent
Falkowski et al.

(10) Patent No.: US 12,036,539 B2
(45) Date of Patent: Jul. 16, 2024

(54) METAL-ORGANIC FRAMEWORK MATERIALS COMPRISING A PYRAZOLYLCARBOXYLATE LIGAND AND METHODS FOR PRODUCTION THEREOF

(71) Applicant: ExxonMobil Technology and Engineering Company, Annandale, NJ (US)

(72) Inventors: Joseph M. Falkowski, Hampton, NJ (US); Yogesh V. Joshi, Bridgewater, NJ (US); Mary S. Abdulkarim, Palisades Park, NJ (US); Simon C. Weston, Annandale, NJ (US)

(73) Assignee: ExxonMobil Technology and Engineering Company, Annandale, NJ (US)

( * ) Notice: Subject to any disclaimer, the term of this patent is extended or adjusted under 35 U.S.C. 154(b) by 172 days.

(21) Appl. No.: 17/621,281

(22) PCT Filed: May 28, 2020

(86) PCT No.: PCT/US2020/034811
§ 371 (c)(1),
(2) Date: Dec. 21, 2021

(87) PCT Pub. No.: WO2021/006964
PCT Pub. Date: Jan. 14, 2021

(65) Prior Publication Data
US 2022/0370992 A1    Nov. 24, 2022

Related U.S. Application Data

(60) Provisional application No. 62/871,818, filed on Jul. 9, 2019.

(51) Int. Cl.
*B01J 31/16*     (2006.01)
*B01J 35/61*     (2024.01)
(Continued)

(52) U.S. Cl.
CPC ......... *B01J 31/1691* (2013.01); *B01J 35/617* (2024.01); *B01J 35/618* (2024.01);
(Continued)

(58) Field of Classification Search
None
See application file for complete search history.

(56) References Cited

U.S. PATENT DOCUMENTS

2008/0184883 A1\* 8/2008 Zhou ................ B01J 20/226
                                                                95/138
2012/0297982 A1\* 11/2012 Dinca ............... B01J 20/30
                                                                428/641
(Continued)

FOREIGN PATENT DOCUMENTS

KR    2015-0088209         7/2015    ............... C07F 1/08

OTHER PUBLICATIONS

Tu et al. ("Ordered Vacancies and Their Chemistry in Metal-OrganicFrameworks", J. Am. Chem. Soc. 2014, 136, 14465-14471). (Year: 2014).\*

(Continued)

*Primary Examiner* — Ali Z Fadhel

(57) ABSTRACT

Metal-organic framework materials (MOFs) are highly porous entities comprising a multidentate organic ligand coordinated to multiple metal centers. MOFs having ambient condition stability may comprise a plurality of metal clusters comprising one or more $M_4O$ clusters (M is a metal), and a plurality of 4-pyrazolecarboxylate ligands coordinated to the plurality of metal clusters to define an at least partially crystalline network structure having a plurality of internal pores. The MOFs may have a Pa3 symmetry, which upon activation may convert into Fm3m symmetry. Methods for synthesizing the MOFs may comprise combining a metal source, such as a preformed metal cluster, with (Continued)

4-pyrazolecarboxylic acid, and reacting the preformed metal cluster with the 4-pyrazolecarboxylic acid to form a MOF having an at least partially crystalline network structure with a plurality of internal pores defined therein and comprising a plurality of metal clusters coordinated to a multidentate organic ligand comprising 4-pyrazolecarboxylate.

23 Claims, 12 Drawing Sheets

(51) Int. Cl.
    *B01J 35/63* (2024.01)
    *B01J 35/64* (2024.01)
    *B01J 37/04* (2006.01)
    *B01J 37/30* (2006.01)
    *C07C 5/03* (2006.01)
    *C07F 3/06* (2006.01)

(52) U.S. Cl.
    CPC ........... *B01J 35/633* (2024.01); *B01J 35/635* (2024.01); *B01J 35/643* (2024.01); *B01J 35/647* (2024.01); *B01J 37/04* (2013.01); *B01J 37/30* (2013.01); *C07C 5/03* (2013.01); *C07F 3/06* (2013.01); *B01J 2231/645* (2013.01); *B01J 2531/0205* (2013.01); *B01J 2531/0211* (2013.01); *B01J 2531/0238* (2013.01); *B01J 2531/26* (2013.01); *B01J 2531/72* (2013.01); *B01J 2531/845* (2013.01); *B01J 2531/847* (2013.01); *C07C 2531/22* (2013.01)

(56) References Cited

U.S. PATENT DOCUMENTS

2020/0147587 A1\* 5/2020 Yaghi ................ B01J 20/226
2020/0291045 A1\* 9/2020 Peedikakkal ...... C08G 73/0266

OTHER PUBLICATIONS

Betard, A. et al. (2012) "Assessing the Adsorption Selectivity of Linker Functionalized, Moisture-Stable Metal-Organic Framework Thin Films by Means of an Environment-Controlled Quartz Crystal Microbalance," *Chem. Commun.*, v.48, pp. 10493-10495.
Fu, H.-R. et al. (2015) "A Stable Zinc-4-Carboxypyrazole Framework with High Uptake and Selectivity of Light Hydrocarbons," *Dalton Trans.*, v.44, p. 2893.
Gordon, M. R. et al. (1983) "Preparation and properties of tetrazinc µ4-oxohexa-µ-carboxylates (basic zinc carboxylates)," *Can. J. Chem.*, v.61, pp. 1218-1221.
Heering, C. et al. (2013) "Bifuntional Pyrazolate-Carboxylate Ligands for Isoreticular Cobalt and Zinc M0F-5 Analogs with Magnetic Analysis of the { Co4([mu]4-0) } Node," *Crystengcomm*, v.15(45), pp. 9757.
Kaye, S. S. et al. (2007) "Impact of Preparation and Handling on the Hydrogen Storage Properties of $Zn_4O(1,4$-benzenedicarboxylate$)_3$ (MOF-5)," *J. Am. Chem. Soc.*, v.129, pp. 14176-14177.
Lu, Lin et al. (2018) "Flower-Like Zn0-Assisted One-Pot Encapsulation of Noble Metal Nanoparticles Supported Catalysts with ZIFs," *Applied Surface Science*, v.433, pp. 602-609.
Montoro, C. et al. (2011) "Capture of Nerve Agents and Mustard Gas Analogues by Hydrophobic Robust MOF-5 Type Metal-Organic Frameworks," *J. Am. Chem. Soc.*, v.133(31), pp. 11888-11891.
Tu, B. et al, (2014) "Ordered Vacancies and Their Chemistry in Metal-Organic Frameworks," *J. Am. Chem. Soc.*, v.136(41), pp. 14465-14471.

\* cited by examiner

METAL-ORGANIC FRAMEWORK MATERIALS COMPRISING A PYRAZOLYLCARBOXYLATE LIGAND AND METHODS FOR PRODUCTION THEREOF

CROSS REFERENCE TO RELATED APPLICATIONS

This application is a national stage filing of Patent Cooperation Treaty Application No. PCT/US2020/034811, filed May 28, 2020, which claimed priority to U.S. Provisional Application No. 62/871,818, filed Jul. 9, 2019.

FIELD

The present disclosure relates to metal-organic framework materials (MOFs) formed from a pyrazolylcarboxylate ligand.

BACKGROUND

MOFs are a relatively new class of highly porous network materials. In contrast to zeolites, which are purely inorganic in character, MOFs comprise metal ions or clusters interconnected by multidentate organic ligands that function as "struts" bridging the metal ions or clusters together in an extended one-, two-, or three-dimensional coordination network structure (e.g., as a coordination polymer). MOFs offer a high degree of structural and functional tunability which result from the ability to modulate and control the structure of both the organic competent and, to a lesser extent, the network topology. Such features are not generally available with other conventional porous materials. MOFs are characterized by low densities, high internal surface areas, and pores and channels that are tunable through selection of the multidentate organic ligand and the metal or metal source used during synthesis.

MOF-5, also known as IRMOF-1, having a general formula of $Zn_4O(1,4\text{-benzenedicarboxylate})_3$, is the prototypical example of a MOF and was developed nearly 20 years ago. This material and its isoreticular materials (i.e., materials having the same topology) exhibit high pore volumes and high surface areas and have been explored for use in applications taking advantage of these features. However, the long-term performance and stability of these MOFs under ambient moisture conditions has not been reliably established.

MOFs have been investigated extensively for applications in gas storage, gas and liquid separation, sensing, catalysis, drug delivery, and waste remediation, among others. The wide array of potential applications for MOFs stems from the nearly infinite combination of multidentate organic ligands and metal sources available for synthesizing MOFs. In particular, the prospective ability to control the porosity, composition, and functionality of MOFs through selection of components, functionalization, or post-synthetic modifications, makes MOFs promising candidates towards providing stable materials specifically designed for specific applications.

One of the challenges in designing porous network materials, such as MOFs, is the large number of possible coordination environments for any given metal ion. Thus, it is desirable to prepare MOFs having known geometries with respect to various metal-containing nodes. Additionally, it is desirable to provide MOFs via syntheses that are more reproducible and feature higher yields while also allowing for more varied synthetic conditions and resulting in different structural behaviors.

SUMMARY

In some embodiments, the present disclosure provides MOFs comprising a plurality of metal clusters comprising one or more $M_4O$ clusters, wherein M is a metal; and a plurality of multidentate organic ligands coordinated to the plurality of metal clusters to define an at least partially crystalline network structure having a plurality of internal pores, the multidentate organic ligand comprising 4-pyrazolecarboxylate, wherein the at least partially crystalline network structure has an x-ray powder diffraction pattern comprising characteristic diffraction peaks consistent with a Pa3 symmetry.

In some or other embodiments, the present disclosure provides MOFs comprising a plurality of metal clusters comprising one or more $M_4O$ clusters, wherein M is a metal; and a plurality of multidentate organic ligands coordinated to the plurality of metal clusters to define an at least partially crystalline network structure having a plurality of internal pores, the multidentate organic ligand comprising 4-pyrazolecarboxylate, wherein the at least partially crystalline network structure has an x-ray powder diffraction pattern comprising characteristic diffraction peaks of at least 8.91, 9.96, 10.9, and 12.6 (all ±5%) degree 2-theta (° 2θ).

In some embodiments, methods for synthesizing MOFs may comprise: combining a metal source with 4-pyrazolecarboxylic acid; and reacting the metal source with the 4-pyrazolecarboxylic acid to form a MOF having an at least partially crystalline network structure with a plurality of internal pores defined therein and comprising a plurality of metal clusters coordinated to a multidentate organic ligand comprising 4-pyrazolecarboxylate, the plurality of metal clusters comprising one or more $M_4O$ clusters, wherein M is a metal; wherein the at least partially crystalline network structure has an x-ray powder diffraction pattern comprising characteristic diffraction peaks of at least 8.91, 9.96, 10.9, and 12.6 (all ±5%) degree 2-theta (° 2θ).

In some or other embodiments, methods of the present disclosure may comprise: combining a preformed metal cluster with 4-pyrazolecarboxylic acid; and reacting the preformed metal cluster with the 4-pyrazolecarboxylic acid to form a metal-organic framework material having an at least partially crystalline network structure with a plurality of internal pores defined therein and comprising a plurality of metal clusters coordinated to the 4-pyrazolecarboxylate, the plurality of metal clusters comprising one or more $M_4O$ clusters, wherein M is a metal; wherein the at least partially crystalline network structure has an x-ray powder diffraction pattern comprising characteristic diffraction peaks consistent with a Pa3 symmetry.

In still other embodiments, methods of the present disclosure may comprise: contacting a mixture comprising one or more chemical species with a metal-organic framework material comprising: a plurality of metal clusters comprising one or more $M_4O$ clusters, wherein M is a metal; and a plurality of multidentate organic ligands coordinated to the plurality of metal clusters to define an at least partially crystalline network structure having a plurality of internal pores, the multidentate organic ligand comprising 4-pyrazolecarboxylate, wherein the at least partially crystalline network structure has an x-ray powder diffraction pattern comprising characteristic diffraction peaks of at least 8.91, 9.96, 10.9, and 12.6 (all ±5%) degree 2-theta (° 2θ); and sorbing at least a portion of the one or more chemical species into at least a portion of the internal pores.

In still other embodiments, methods of the present disclosure may comprise: providing a catalyst precursor comprising a reaction product of 4-pyrazolecarboxylic acid and a preformed metal cluster, the reaction product being a metal-organic framework material having an at least partially crystalline network structure with a plurality of internal pores defined therein and comprising a plurality of metal clusters comprising one or more $M_4O$ clusters, wherein M is a metal, coordinated to the 4-pyrazolecarboxylate; wherein the at least partially crystalline network structure has an x-ray powder diffraction pattern comprising characteristic diffraction peaks consistent with a Pa3 symmetry; exposing the catalyst precursor to a reducing agent to form an activated catalyst; contacting the activated catalyst with an olefin; and hydrogenating the olefin while the olefin contacts the activated catalyst.

BRIEF DESCRIPTION OF THE DRAWINGS

The following figures are included to illustrate certain aspects of the present disclosure, and should not be viewed as exclusive embodiments. The subject matter disclosed is capable of considerable modifications, alterations, combinations, and equivalents in form and function, as will occur to one of ordinary skill in the art and having the benefit of this disclosure.

DETAILED DESCRIPTION

Figure 1:
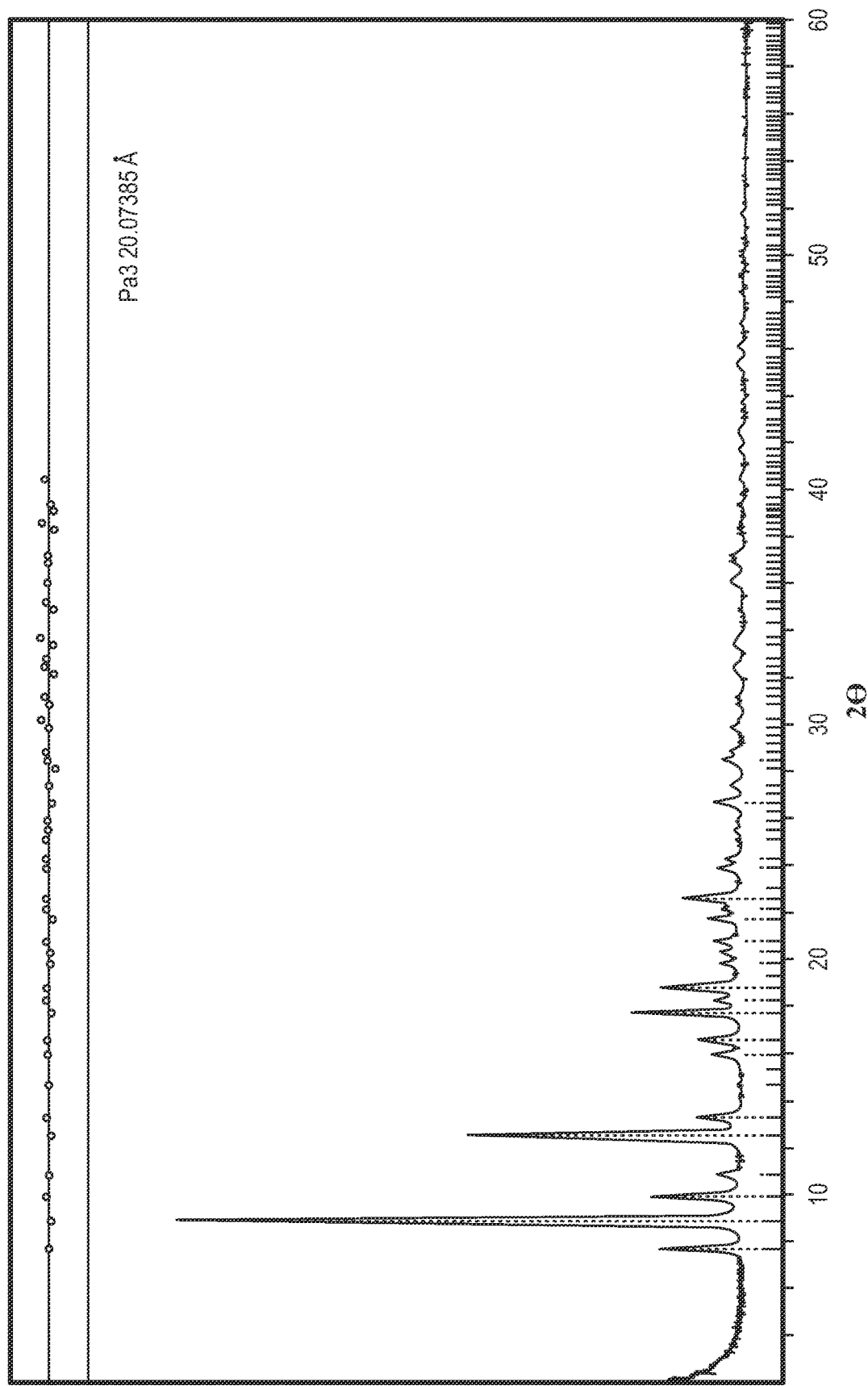
FIG. 1 shows an x-ray powder diffraction pattern for the MOF obtained in Example 1A.

The present disclosure relates to MOFs formed from a pyrazolylcarboxylate ligand.

As discussed in brief above, MOFs may be synthesized by reacting a multidentate organic ligand with a suitable metal source to form a crystalline or partially crystalline network structure having a plurality of internal pores. The network structure may constitute a coordination polymer in some instances. The structure and properties of MOFs are tunable through selection of the multidentate organic ligand and the metal or metal source. As highly porous materials, MOFs can selectively adsorb and/or separate different types of gases, molecules or other chemical entities. As such, MOFs have potential applications including gas storage and separation. However, the chemical stability of many conventional MOFs hamper the ability to take advantage of their porous structure.

The present disclosure provides MOFs comprising multidentate organic ligands that are readily available and possess differing binding sites. In particular, the multidentate organic ligands employed in the present disclosure comprise a pyrazolyl moiety as a first binding site and carboxylate moiety as a second binding site. The pyrazolyl moiety of the multidentate organic ligands may include various substituents. Surprisingly, the multidentate organic ligands described herein may afford materials having network structures featuring a cubic topology and exhibiting dynamic solvation states resulting in changes in symmetry of the solvated and unsolvated materials. The incorporation of the pyrazolylcarboxylate ligand also imparts water stability, increased ability for post-synthesis modification, and increased ease of synthesis through cluster-based approach compared to those of MOF-5. Surprisingly, MOF's synthesized according to the disclosure herein have x-ray powder diffractions differing significantly from those synthesized using the same pyrazolecarboxylate ligand under different synthetic procedures (Tu et al., J. Am. Chem. Soc., 2014, 136, 14465), indicating that different MOF structures are formed using the metal sources disclosed herein.

In particular embodiments, the multidentate organic ligands of the present disclosure may comprise 4-pyrazolecarboxylate. As discussed further herein, this multidentate organic ligand may react with various metal sources to form MOFs having advantageous properties. More specific embodiments of such MOFs may comprise a plurality of zinc centers or zinc clusters and a 4-pyrazolecarboxylate multidentate organic ligand coordinated to the plurality of zinc centers or zinc clusters via at least one binding site to define an at least partially crystalline network structure having a plurality of internal pores.

Surprisingly, 4-pyrazolecarboxylate and similar multidentate organic ligands may form MOFs having variable network structures depending upon the metal source and reaction conditions (e.g., concentration, temperature and time) that are used. In some instances, a preformed metal cluster, such as $Zn_4O(2,2\text{-dimethylbutanote})_6$ ($Zn_4O(DMBA)_6$) or similar metal carboxylate clusters, may be particularly suitable for reaction with the foregoing pyrazolylcarboxylate ligand to form MOFs. While preformed metal clusters may be particularly desirable metal sources for promoting formation of MOFs, other metal sources may also be satisfactorily used when forming MOFs without a dynamic solvation state. The ability of the pyrazolylcarboxylate ligand described herein to form stable MOFs is believed to result from the structural strength of robust metal-ligand bonding, while still positioning the binding sites effectively to promote large, cubic pores via coordination of metal clusters to the pyrazolate and carboxylate moieties.

In addition to the foregoing, MOFs synthesized using the multidentate organic ligands described herein may undergo exchange with other metals to replace at least a portion of the metal atoms at the metal centers or metal clusters with one or more different metals. The one or more different metals may be introduced for any purpose, such as for conveying additional structural stabilization or for promoting a catalytic reaction. Minimal structural reorganization occurs when metal exchange takes place in many cases.

Before describing the various embodiments of the present disclosure in further detail, a listing of terms follows to aid in better understanding the present disclosure.

All numerical values within the detailed description and the claims herein are modified by "about" or "approximately" with respect to the indicated value, and take into account experimental error and variations that would be expected by a person having ordinary skill in the art. Unless otherwise indicated, room temperature is about 25° C.

As used in the present disclosure and claims, the singular forms "a," "an," and "the" include plural forms unless the context clearly dictates otherwise.

The term "and/or" as used in a phrase such as "A and/or B" herein is intended to include "A and B," "A or B," "A", and "B."

For the purposes of the present disclosure, the new numbering scheme for groups of the Periodic Table is used. In said numbering scheme, the groups (columns) are numbered sequentially from left to right from 1 through 18, excluding the f-block elements (lanthanides and actinides).

As used in the present disclosure and claims, Me is methyl, Et is ethyl, Pr is propyl, cPr is cyclopropyl, nPr is n-propyl, iPr is isopropyl, Bu is butyl, nBu is normal butyl, iBu is isobutyl, sBu is sec-butyl, tBu is tert-butyl, Cy is cyclohexyl, Oct is octyl, Ph is phenyl, and Bn is benzyl.

The term "hydrocarbon" refers to a class of compounds having hydrogen bound to carbon, and encompasses (i) saturated hydrocarbon compounds, (ii) unsaturated hydrocarbon compounds, and (iii) mixtures of hydrocarbon compounds (saturated and/or unsaturated), including mixtures of hydrocarbon compounds having different numbers of carbon atoms. The term "$C_n$" refers to hydrocarbon(s) or a hydrocarbyl group having n carbon atom(s) per molecule or group, wherein n is a positive integer. Such hydrocarbon compounds may be one or more of linear, branched, cyclic, acyclic, saturated, unsaturated, aliphatic, or aromatic, with optional substitution being present in some cases.

The terms "hydrocarbyl" and "hydrocarbyl group" are used interchangeably herein. The term "hydrocarbyl group" refers to any $C_1$-$C_{100}$ hydrocarbon group bearing at least one unfilled valence position when removed from a parent compound. Suitable "hydrocarbyl" and "hydrocarbyl groups" may be optionally substituted. The term "hydrocarbyl group having 1 to about 100 carbon atoms" refers to an optionally substituted moiety selected from a linear or branched $C_1$-$C_{100}$ alkyl, a $C_3$-$C_{100}$ cycloalkyl, a $C_6$-$C_{100}$ aryl, a $C_2$-$C_{100}$ heteroaryl, a $C_1$-$C_{100}$ alkylaryl, a $C_7$-$C_{100}$ arylalkyl, and any combination thereof.

The term "substituted" refers to replacement of at least one hydrogen atom or carbon atom of a hydrocarbon or hydrocarbyl group with a heteroatom or heteroatom functional group. Heteroatoms may include, but are not limited to, B, O, N, S, P, F, Cl, Br, I, Si, Pb, Ge, Sn, As, Sb, Se, and Te. Heteroatom functional groups that may be present in substituted hydrocarbons or hydrocarbyl groups include, but are not limited to, functional groups such as O, S, S=O, $S(=O)_2$, $NO_2$, F, Cl, Br, I, $NR_2$, OR, SeR, TeR, $PR_2$, $AsR_2$, $SbR_2$, SR, $BR_2$, $SiR_3$, $GeR_3$, $SnR_3$, $PbR_3$, where R is a hydrocarbyl group or H. Suitable hydrocarbyl R groups may include alkyl, alkenyl, alkynyl, aryl, heteroaryl, cycloalkyl, heterocyclyl, and the like, any of which may be optionally substituted.

The term "optionally substituted" means that a hydrocarbon or hydrocarbyl group may be unsubstituted or substituted. For example, the term "optionally substituted hydrocarbyl" refers to replacement of at least one hydrogen atom or carbon atom in a hydrocarbyl group with a heteroatom or heteroatom functional group. Unless otherwise specified, any of the hydrocarbyl groups herein may be optionally substituted.

The terms "linear" or "linear hydrocarbon" refer to a hydrocarbon or hydrocarbyl group having a continuous carbon chain without side chain branching, in which the continuous carbon chain may be optionally substituted.

The terms "cyclic" or "cyclic hydrocarbon" refer to a hydrocarbon or hydrocarbyl group having a closed carbon ring, which may be optionally substituted.

The terms "branched" or "branched hydrocarbon" refer to a hydrocarbon or hydrocarbyl group having a linear carbon chain or a closed carbon ring, in which a hydrocarbyl side chain extends from the linear carbon chain or the closed carbon ring. Optional substitution may be present in the linear carbon chain, the closed carbon ring, and/or the hydrocarbyl side chain.

The terms "saturated" or "saturated hydrocarbon" refer to a hydrocarbon or hydrocarbyl group in which all carbon atoms are bonded to four other atoms, with the exception of an unfilled valence position being present upon a carbon atom in a hydrocarbyl group.

The terms "unsaturated" or "unsaturated hydrocarbon" refer to a hydrocarbon or hydrocarbyl group in which one or more carbon atoms are bonded to less than four other atoms, exclusive of an open valence position upon carbon being present. That is, the term "unsaturated" refers to a hydrocarbon or hydrocarbyl group bearing one or more double and/or triple bonds, with the double and/or triple bonds being between two carbon atoms and/or between a carbon atom and a heteroatom.

The terms "aromatic" or "aromatic hydrocarbon" refer to a hydrocarbon or hydrocarbyl group having a cyclic arrangement of conjugated pi-electrons that satisfies the Hückel rule.

The term "alkyl" refers to a hydrocarbyl group having no unsaturated carbon-carbon bonds, and which may be optionally substituted.

The terms "alkene" and "olefin" are used synonymously herein. Similarly, the terms "alkenic" and "olefinic" are used synonymously herein. Unless otherwise noted, all possible geometric isomers are encompassed by these terms.

The term "aryl" is equivalent to the term "aromatic" as defined herein. The term "aryl" refers to both aromatic compounds and heteroaromatic compounds, which may be optionally substituted. Both mononuclear and polynuclear aromatic compounds are encompassed by these terms.

The terms "heteroaryl" and "heteroaromatic" refer to an aromatic ring containing a heteroatom and which satisfies the Hückel rule.

Examples of aromatic hydrocarbyl groups include, but are not limited to, phenyl, tolyl, xylyl, naphthyl, and the like. Heteroaryl and polynuclear heteroaryl groups may include, but are not limited to, pyridyl, quinolinyl, isoquinolinyl, pyrimidinyl, quinazolinyl, acridinyl, pyrazinyl, quinoxalinyl, imidazolyl, benzimidazolyl, pyrazolyl, benzopyrazolyl, oxazolyl, benzoxazolyl, isoxazolyl, benzisoxazolyl, imidazolinyl, thiophenyl, benzothiophenyl, furanyl and benzofuranyl. Polynuclear aryl groups may include, but are not limited to, naphthalenyl, anthracenyl, indanyl, indenyl, and tetralinyl.

As used herein, the term "multidentate" refers to a compound having two or more potential sites for coordinating a metal center. Accordingly, the term "multidentate" encompasses bidentate, tridentate, tetradentate, and higher denticity ligands.

The term "metal center" refers to a single metal atom or metal ion, or a group of metal atoms and/or metal ions to which a ligand coordinatively bonded.

The term "metal cluster" refers to a group of metal atoms and/or metal ions bonded together.

The term "secondary building unit" refers to a metal cluster to which two or more multidentate organic ligands are coordinatively bonded. For example, a secondary building unit may have the formula $M_4O$ and may be coordinated to multidentate organic ligands, such as carboxylate groups, to form MOFs having multi-metal nuclear carboxylate clusters of formula $M_4O(CO_2)_6$. The cluster $M_4O$ may also be coordinated by bidentate groups including carboxylate or hydrazyl groups to form MOFs.

The term "preformed metal cluster" refers to a grouping of multiple metal atoms and/or metal ions and one or more ligands, in which the grouping is synthesized prior to being combined with another material to form a MOE.

The term "at least partially crystalline" means that a substance exhibits an x-ray powder diffraction pattern.

The term "binding site" refers to a chemical entity capable of coordinating a metal center by a metal-ligand bond.

The term "activation" refers to the removal of solvent molecules or molecular charge balancing species by heating and/or evacuation.

Accordingly, MOFs of the present disclosure may comprise: a plurality of metal centers or metal clusters and a plurality of multidentate organic ligands coordinated to the plurality of metal centers or metal clusters to define an at least partially crystalline network structure having a plurality of internal pores. The multidentate organic ligands comprise 4-pyrazolecarboxylate.

The MOFs disclosed herein may differ morphologically from previous MOFs incorporating 4-pyrazolecarboxylate (see Tu et al., J. Am. Chem. Soc., 2014, 136, 14465) when a suitable metal source is used. In particular, MOFs disclosed herein may feature an at least partially crystalline network structure exhibiting characteristic x-ray powder diffraction peaks of at least 8.91, 9.96, 10.9, and 12.6 (all ±5%) degree 2-theta (2θ). Other distinguishing characteristics may include the space group of the MOF (space group Pa3 in the case of the MOFs disclosed herein). The MOFs may transition between space groups upon solvation or desolvation.

Formula 1 below shows the chemical structure of 4-pyrazolecarboxylic acid, which is capable of becoming incorporated in MOFs of the present disclosure as a multidentate organic ligand.

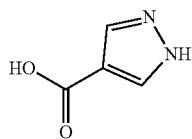

Formula I

The identity of the metal centers or metal clusters that may be present in the MOFs disclosed herein is not considered to be particularly limited. In some embodiments, at least a portion of the plurality of metal clusters may comprise one or more metal centers having a tetrahedral geometry. In some embodiments, at least a portion of the plurality of metal centers or metal clusters may comprise a divalent metal. Trivalent metals may also be suitably included in some instances, either alone or in combination with one or more divalent metals. Suitable divalent metals that may be present in the MOFs disclosed herein include, for example, zinc, cobalt, nickel, copper, iron, chromium, manganese, or any combination thereof. The metal(s) comprising the plurality of metal centers or metal clusters may be introduced when reacting a suitable metal source with the multidentate organic ligands disclosed above, or at least a portion of the metal(s) in the metal centers or metal clusters may be introduced via an exchange reaction after forming the at least partially crystalline network structure defining the MOF. In particular embodiments, the metal clusters may be in the form of one or more $M_4O$ clusters, wherein M is a metal.

In some embodiments, a preformed metal cluster may be a suitable metal source for forming the MOFs disclosed herein. Determination of the presence of a network structure and crystallinity thereof, including a determination of whether a particular network structure is related to another network structure, may be performed by x-ray powder diffraction, as described elsewhere herein. One example of a suitable preformed metal cluster that may be used to promote formation of a MOF with the multidentate organic ligands described herein is a zinc cluster described by the formula $Zn_4O(2,2\text{-dimethylbutanoic acid})_6$ ($Zn_4O(DMBA)_6$).

Accordingly, still more specific MOFs of the present disclosure may comprise a plurality of metal clusters, and 4-pyrazolecarboxylate coordinated to the plurality of metal clusters to define an at least partially crystalline network structure having a plurality of internal pores, wherein the plurality of metal clusters comprises one or more $M_4O$ clusters. In yet still more specific examples, such MOB may comprise a plurality of zinc clusters, and 4-pyrazolecarboxylate coordinated to the plurality of zinc clusters to define an at least partially crystalline network structure having a plurality of internal pores. Such MOFs may be defined by the characteristic x-ray powder diffraction peaks specified above. In some or other more specific embodiments, the MOFs of the present disclosure comprising a plurality of zinc clusters may further comprise a plurality of nickel centers also coordinated to the 4-pyrazolecarboxylate ligand via at least one binding site. The nickel centers may be introduced through a metal exchange reaction with at least a portion of the zinc.

The MOFs formed according to the disclosure herein may be characterized in terms of their internal porosity, particularly MOFs formed from 4-pyrazolecarboxylate as a multidentate organic ligand. The MOFs of the present disclosure may include micropores, mesopores, macropores and any combination thereof. Micropores are defined herein as having a pore size of about 2 nm or below, and mesopores are defined herein as having a pore size from about 2 nm to about 50 nm. Determination of microporosity and/or mesoporosity may be determined by analysis of the nitrogen adsorption isotherms at 77 K, as will be understood by one having ordinary skill in the art. Internal pore volumes and other morphological features of the MOFs may similarly be determined from the nitrogen adsorption isotherms, as also will be understood by one having ordinary skill in the art. As a non-limiting example, MOFs formed according to the present disclosure may exhibit pore volumes up to 0.582 cc/g and a micropore volume of up to 0.45 cc/g. Total surface areas of 1257 $m^2/g$ are achievable with micropore surface areas of 1181 $m^2/g$. In these embodiments, pore radii of about 4.1 Å are identifiable by DFT analysis of nitrogen adsorption isotherms. In some embodiments, in addition to these micropores, mesopores with a pore radii of about 20 Å may be identifiable. The contribution of the total pore volume by these mesopores can be significant, providing approximately half of the total pore volume. Total pore volumes of up to 0.64 cc/g may be observed, with a micropore volume contributing 0.34 cc/g to this total. In these highly mesoporous materials, surface areas of up to 906 m$^2$/g may be observed, and up to 717 m$^2$/g of that being micropore surface area.

The metal-organic frameworks of the current disclosure, as synthesized, may exhibit an x-ray powder diffraction pattern consistent with a cubic unit cell having systematic absences of a Pa3 space group. It is understood that under the analysis conditions, other space groups with similar symmetry operators and systematic absences may exist that are indistinguishable via lab-based x-ray diffraction techniques.

Upon activation (i.e., removal of solvents via heating and/or evacuation), the x-ray powder diffraction peaks at 7.73, 9.95 and 10.9° 2θ are all attenuated and may disappear entirely. In addition to the disappearance of these peaks, peaks at ~14.5 and 19° 2θ appear. Combined, the symmetry of the observed powder pattern is consistent with a higher symmetry, particularly a Fm3m unit cell. This change in symmetry is reversible, with the introduction of solvents such as dimethylformamide or ethanol resulting in a reemergence of the apparent Pa3 space group. Drying again yields the Fm3m space group. On a structural level, the conversion of the material between Pa3 and Fm3m may result in the loss of symmetry equivalence of one of the four structural zinc cations that comprise the zinc cluster secondary building unit.

Methods are also described herein for synthesizing the MOFs of the present disclosure. Some syntheses may be advantageously conducted with a preformed metal cluster as a metal source, as discussed above, but other metal sources, including some simple metal salts may also be used. Advantageously, the metal source may be selected such that MOB having related, but slightly different network structures, are obtained. As such, selection of the metal source used for synthesizing the MOFs disclosed herein may allow tailoring of the network structure to be realized for compatibility with particular applications.

Accordingly, certain methods of the present disclosure may comprise: combining a metal source with 4-pyrazolecarboxylic acid, and reacting the metal source with the 4-pyrazolecarboxylic acid to form a metal-organic framework material having an at least partially crystalline network structure with a plurality of internal pores defined therein and comprising a plurality of metal centers or metal clusters coordinated to a multidentate organic ligand comprising 4-pyrazolecarboxylate. Such MOB may be defined by the characteristic x-ray powder diffraction peaks specified above, particularly those characteristic of Pa3 symmetry. In more specific embodiments, the metal source may be a preformed metal cluster, such as a preformed metal cluster comprising zinc, and more particularly $Zn_4O(2,2$-dimethylbutanoate$)_6$ or a similar metal carboxylate cluster. MOFs prepared using a metal carboxylate cluster may be advantageous in terms of directing the structure to provide more reproducible and higher yielding syntheses while also allowing for more varied synthetic conditions. Metal carboxylate clusters may also afford different structural behaviors that may not be observable when using other metal sources.

In some embodiments, the removal of a residual ligand, a metal salt or a solvent incorporated in the internal pores from the MOFs disclosed herein is observable in the x-ray diffraction pattern of the MOFs as a change in symmetry. For example, upon removal of residual ligand, a metal salt or a solvent, the MOFs of the present disclosure may change from a cubic m-3 Laue class to a cubic m-3m Laue class. More particularly, the change in symmetry upon solvation and/or desolvation of the MOFs disclosed herein is from a cubic Pa3 space group to a cubic Fm-3m space groups. Without being bound by theory or mechanism, the ability to change symmetry is believed to be related to the formation of a kinetic product able to undergo this symmetry change as a result of using a preformed zinc cluster, as opposed to a thermodynamic product resulting from using zinc salts.

In some embodiments, residual ligands, such as 2,2-dimethylbutanoic acid or a salt thereof, or a metal salt, or a solvent, may be thermally removed from the plurality of internal pores. Sufficiently elevated temperatures may either volatilize the residual ligands above their boiling point or promote thermal decomposition in some cases. In illustrative embodiments, thermal removal of the residual ligands may take place at a temperature of at least about 100° C., or at least about 150° C., or at least about 200° C., or at least about 450° C. Selection of a suitable temperature for thermal removal of residual ligands may be dictated by the boiling point of the residual ligands, their thermal stability, and/or the thermal stability of the MOF itself.

Some or other methods of the present disclosure may comprise exchanging at least a portion of a first metal cation comprising the plurality of metal centers or metal clusters for a second metal cation. For example, at least a portion of zinc cations comprising the metal clusters may be exchanged for nickel cations, according to various embodiments of the present disclosure. Metal cations exchange may be affected by contacting the MOFs with a salt solution, for example.

Certain metal-organic framework materials of the present disclosure may have catalytic properties, either by themselves or after catalytic activation in the presence of a suitable activator. One particular example of a catalytic metal-organic framework material may comprise a reaction product of 4-pyrazolecarboxylic acid and a preformed zinc cluster, particularly $Zn_4O(2,2$-dimethylbutanoic acid$)_6$, in which at least a portion of the metal clusters comprise one or more metal centers comprising zinc, and at least a portion of the zinc has been exchanged for a catalytically active metal, such as nickel.

As such, catalyst systems of the present disclosure may comprise a catalyst precursor comprising such metal-organic framework materials, which may be activated through chemical treatment with a reducing agent such as molecular hydrogen. This activated catalyst can then be used to reduce organic olefinic compounds, such as ethylene, to afford the saturated product.

Accordingly, some methods of the present disclosure may comprise, contacting a mixture comprising one or more chemical species with a metal-organic framework material comprising a plurality of metal centers or metal clusters comprising one or more $M_4O$ dusters, wherein M is a metal, and a plurality of multidentate organic ligands coordinated to the plurality of metal centers or metal clusters to define an at least partially crystalline network structure having a plurality of internal pores, the multidentate organic ligand comprise 4-pyrazolecarboxylate, and sorbing at least a portion of the one or more chemical species into at least a portion of the plurality of internal pores. The at least partially crystalline network structure has an x-ray powder diffraction pattern comprising the characteristic diffraction peaks specified above and/or which is consistent with Pa3 symmetry.

Likewise, some or other methods of the present disclosure may comprise providing a catalyst precursor comprising a reaction product of 4-pyrazolecarboxylic acid and a preformed metal cluster, the reaction product being a metal-organic framework material having an at least partially crystalline network structure with a plurality of internal pores defined therein and comprising a plurality of metal clusters comprising one of more $M_4O$ clusters, wherein M is a metal, coordinated to the 4-pyrazolecarboxylic acid; exposing the catalyst precursor to a reducing agent to form an activated catalyst; contacting the activated catalyst with an olefin; and hydrogenating the olefin while the olefin contacts the activated catalyst. The at least partially crystalline network structure has an x-ray powder diffraction pattern including the characteristic x-ray powder diffraction peaks specified above and/or which is consistent, with a Pa3 symmetry.

Embodiments disclosed herein include:

A. MOFs having a 4-pyrazolecarboxylate ligand. The MOFs comprise: a plurality of metal clusters comprising one or more $M_4O$ clusters, wherein M is a metal; and a plurality of multidentate organic ligands coordinated to the plurality of metal clusters to define an at least partially crystalline network structure having a plurality of internal pores, the multidentate organic ligand comprising 4-pyrazolecarboxylate; wherein the at least partially crystalline network structure has an x-ray powder diffraction pattern comprising characteristic diffraction peaks consistent with a Pa3 symmetry.

B. MOFs having a 4-pyrazolecarboxylate ligand and comprising characteristic diffraction peaks. The MOFs comprise: a plurality of metal clusters comprising one or more $M_4O$ clusters, wherein M is a metal; and a plurality of multidentate organic ligands coordinated to the plurality of metal clusters to define an at least partially crystalline network structure having a plurality of internal pores, the multidentate organic ligand comprising 4-pyrazolecarboxylate, wherein the at least partially crystalline network structure has an x-ray powder diffraction pattern comprising characteristic diffraction peaks of at least 8.91, 9.96, 10.9 and 12.6 (all ±5%) degree 2-theta (° 2θ).

C. Methods for making a MOF having a 4-pyrazolecarboxylate ligand. The methods comprise: combining a preformed metal cluster with 4-pyrazolecarboxylic acid; and reacting the preformed metal cluster with the 4-pyrazolecarboxylic acid to form a metal-organic framework material having an at least partially crystalline network structure with a plurality of internal pores defined therein and comprising a plurality of metal clusters coordinated to the 4-pyrazolecarboxylate, the plurality of metal clusters comprising one or more $M_4O$ clusters, wherein M is a metal; wherein the at least partially crystalline network structure has an x-ray powder diffraction pattern comprising characteristic diffraction peaks consistent with a Pa3 symmetry.

D. Methods for making a MOF having a 4-pyrazolecarboxylate ligand and comprising characteristic diffraction peaks. The methods comprise: combining a metal source with 4-pyrazolecarboxylic acid; and reacting the metal source with the 4-pyrazolecarboxylic acid to form a metal-organic framework material having an at least partially crystalline network structure with a plurality of internal pores defined therein and comprising a plurality of metal clusters coordinated to a multidentate organic ligand comprising 4-pyrazolecarboxylate, the plurality of metal clusters comprising one or more $M_4O$ clusters, wherein M is a metal; wherein the at least partially crystalline network structure has an x-ray powder diffraction pattern comprising characteristic diffraction peaks of at least 8.91, 9.96, 10.9 and 12.6 (all ±5%) degree 2-theta (° 2θ).

E. Catalyst methods. The methods comprise: providing a catalyst precursor comprising a reaction product of 4-pyrazolecarboxylic acid and a preformed metal cluster, the reaction product being a metal-organic framework material having an at least partially crystalline network structure with a plurality of internal pores defined therein and comprising a plurality of metal clusters comprising one or more $M_4O$ clusters, wherein M is a metal, coordinated to the 4-pyrazolecarboxylate; wherein the at least partially crystalline network structure has an x-ray powder diffraction pattern comprising characteristic diffraction peaks consistent with a Pa3 symmetry; exposing the catalyst precursor to a reducing agent to form an activated catalyst; contacting the activated catalyst with an olefin; and hydrogenating the olefin while the olefin contacts the activated catalyst.

F. Separation methods. The methods comprise: contacting a mixture comprising one or more chemical species with a metal-organic framework material comprising: a plurality of metal clusters comprising one or more $M_4O$ clusters, wherein M is a metal; and a plurality of multidentate organic ligands coordinated to the plurality of metal clusters to define an at least partially crystalline network structure having a plurality of internal pores, the multidentate organic ligand comprising 4-pyrazolecarboxylate, wherein the at least partially crystalline network structure has an x-ray powder diffraction pattern comprising characteristic diffraction peaks of at least 8.91, 9.96, 10.9 and 12.6 (all ±5%) degree 2-theta (° 2θ); and sorbing at least a portion of the one or more chemical species into at least a portion of the internal pores.

Embodiments A-F may have one or more of the following additional elements in any combination:

Element 1: wherein the at least partially crystalline network structure has a cubic topology.

Element 2: wherein the at least partially crystalline network structure has a Pa3 symmetry.

Element 3: wherein at least a portion of the plurality of metal clusters comprise one or more metal centers having a tetrahedral geometry.

Element 4: wherein at least a portion of the plurality of metal clusters comprise a divalent metal.

Element 5: wherein at least a portion of the plurality of metal clusters comprise zinc, cobalt, nickel, copper, iron, chromium, manganese, or any combination thereof.

Element 6: wherein at least a portion of the plurality of metal clusters comprise zinc.

Element 7: wherein the at least partially crystalline network structure comprises $Zn_4O$ clusters.

Element 8: wherein the metal-organic framework material is a reaction product of a preformed metal cluster and the 4-pyrazolecarboxylate.

Element 9: wherein the preformed metal clusters comprise $Zn_4O(2,2\text{-dimethylbutanoate})_6$.

Element 10: wherein the internal pores have pore diameters in a range of about 6.0 Å to about 40 Å.

Element 11: wherein the internal pores have a pore volume in a range of about 0.4 cc/g to about 0.64 cc/g.

Element 12: wherein the at least partially crystalline network structure has a BET surface area in a range of about 750 $m^2/g$ to about 1300 $m^2/g$.

Element 13: wherein the metal source is a preformed metal cluster.

Element 14: wherein the preformed metal cluster comprises zinc.

Element 15: wherein the metal-organic framework material comprises at least one of a residual ligand, a metal salt or a solvent in at least a portion of the plurality of internal pores.

Element 16: wherein the method further comprises thermally removing the residual ligand, the metal salt, the solvent, or any combination thereof from the plurality of internal pores Element 17: wherein a symmetry of the metal-organic framework material changes upon removing the residual ligand, the metal salt, the solvent, or any combination thereof.

Element 18: wherein the plurality of metal clusters define a plurality of metal centers, the method further comprising: exchanging at least a portion of a first metal comprising the plurality of metal centers for a second metal.

Element 19: wherein the first metal is zinc and the second metal comprises at least one of cobalt, nickel, or manganese.

Element 20: wherein the one or more chemical species comprises hydrogen, nitrogen, a hydrocarbon, or a mixture thereof.

Element 21: wherein at least a portion of the metal clusters comprise zinc, and at least a portion of the zinc is exchanged for a catalytically active metal.

Element 22: wherein the catalytically active metal comprises Ni(II).

Element 23: wherein the reducing agent comprises molecular hydrogen.

By way of non-limiting example, exemplary combinations applicable to A include 4 and 5; 4 and 6; 4 and 7; 4 and 8; 4 and 9; 4, 9 and 10; 4 and 11; 4 and 12; 5 and 6; 5 and 7; 5 and 8; 5 and 9; 5, 9 and 10; 5 and 11; 5 and 12; 6 and 7; 6 and 8; 6 and 9; 6. 9 and 10; 6 and 11; 6 and 12; 7 and 8; 7 and 9; 7, 9 and 10; 7 and 11; 7 and 12; 8 and 9; 8, 9 and 10; 8 and 11; 8 and 12; 9 and 10; 9 and 11; 9 and 12; 9, 10 and 11; 9, 10 and 12; 11 and 12.

Exemplary combinations applicable to B include 1 and 2; 1 and 3; 1 and 4; 1 and 5; 1 and 6; 1 and 7; 1 and 8; 1, 8 and 9; 1 and 10; 1 and 11; 1 and 12; 2 and 3; 2 and 4; 2 and 5; 2 and 6; 2 and 7; 2 and 8; 2, 8 and 9; 2 and 10; 2 and 11; 2 and 12; 3 and 4; 3 and 5; 3 and 6; 3 and 8; 3, 8 and 9; 3 and 10; 3 and 11; 3 and 12; 4 and 5; 4 and 6; 4 and 7; 4 and 8; 4, 8 and 9; 4 and 10; 4 and 11; 4 and 12; 5 and 6; 5 and 7; 5 and 8; 5, 8 and 9; 5 and 10; 5 and 11; 5 and 12; 6 and 7; 6 and 8; 6, 8 and 9; 6 and 10; 6 and 11; 6 and 12; 7 and 8; 7, 8 and 9; 7 and 10; 7 and 11; 7 and 12; 8 and 9; 8 and 10; 8 and 11; 8 and 12; 8, 9 and 10; 8, 9 and 11; 8, 9 and 12; 10 and 11; 10 and 12; 11 and 12.

Exemplary combinations applicable to C include 9 and 14; 9 and 15; 9, 15 and 16; 9, 15 and 17; 9, 16 and 17; 9 and 18; 9 and 19; 14 and 15; 14, 15 and 16; 14, 15 and 17; 14, 16 and 17; 14 and 18; 14 and 19; 15 and 16; 15, 16 and 17; 15 and 18; 15 and 19; 18 and 19.

Exemplary combinations applicable to D include 3 and 13; 3, 13 and 14; 3, 9 and 13; 3 and 15; 3 and 16; 3, 16 and 17; 3 and 18; 3 and 19; 13 and 14; 9 and 13, 13 and 15; 13, 15 and 16; 13 and 17; 13 and 18; 13 and 19; 9 and 14; 14 and 15; 14, 15 and 16; 14 and 17; 14 and 18; 14 and 19; 15 and 16; 15, 16 and 17; 15 and 18; 15 and 19; 15, 16 and 18; 15, 16 and 19; 17 and 18; 17 and 19; 18 and 19.

Exemplary combinations applicable to E include 21 and 22; 21 and 23; 22 and 23.

To facilitate a better understanding of the embodiments described herein, the following examples of various representative embodiments are given. In no way should the following examples be read to limit, or to define, the scope of the present disclosure.

Examples x-Ray powder diffraction patterns in the examples below were obtained using Cu K-α radiation.

BET surface areas in the examples below were determined from $N_2$ adsorption isotherms obtained at 77 K. $N_2$ adsorption isotherms were measured using an Autosorb IQ3 analyzer (Quantachrome) at 77 K. Before measurement, the samples were degassed at 180° C. to a constant pressure of $10^{-5}$ torr for 12 hours. The surface area was then measured by the amount of $N_2$ adsorbed onto the surface of the sample. Regression analysis was subsequently applied to the data, resulting in an isotherm. The isotherms were further analyzed to calculate the micropore volume and other quantities.

Example 1A: Metal-Organic Framework Synthesis. 4-pyrazolecarboxylic acid (1.7 g) was dissolved in 400 mL of a 20 vol. % solution of water in ethanol. This solution was heated to 60° C. and 5.74 g $Zn_4O(2,2\text{-dimethylbutanoate})_6$ (2,2-dimethylbutanoate=DMBA) was added as a solid. Synthesis of $Zn_4O(DMBA)_6$ was accomplished by literature methods described in M. R. Gordon, et al., "Preparation and properties of tetrazine $\mu_4$-oxohexa-$\mu$-carboxylates (basic zinc carboxylates)," Can. J. Chem., 1983, pp. 1218-1221, 61. The reaction began to form solids immediately and was allowed to stir overnight at 60° C. The solids were then isolated by centrifugation and washed with N,N-dimethylformamide (DMF). The isolated solids were re-suspended in DMF and heated to 60° C. and stirred for 4 additional hours. The solids were isolated by centrifugation, and then washed sequentially with toluene and cyclohexane. A dry powder was isolated by either letting the cyclohexane-wet solids dry at room temperature, or by freezing the solid in a bath of sufficiently low enough temperature to freeze the suspension of MOF in cyclohexane and then applying a vacuum to remove the cyclohexane via sublimation (freeze drying).

Example 1B: Metal-Organic Framework synthesis. A synthesis identical to that of Example 1A was carried out except substituting the ethanol/water solvent for a 70/30 volume ratio of N,N-dimethylformamide and water. The solids were then isolated by centrifugation and washed with N,N-dimethylformamide (DMF). The isolated solids were re-suspended in DMF and heated to 60° C. and stirred for 4 additional hours. The solids were isolated by centrifugation, and then washed sequentially with ethanol and cyclohexane. A dry powder was isolated by either letting the cyclohexane-wet solids dry at room temperature, or by freezing the solid in a bath of sufficiently low enough temperature to freeze the suspension of MOF in cyclohexane and then applying a vacuum to remove the cyclohexane via sublimation (freeze drying).

Figure 7:
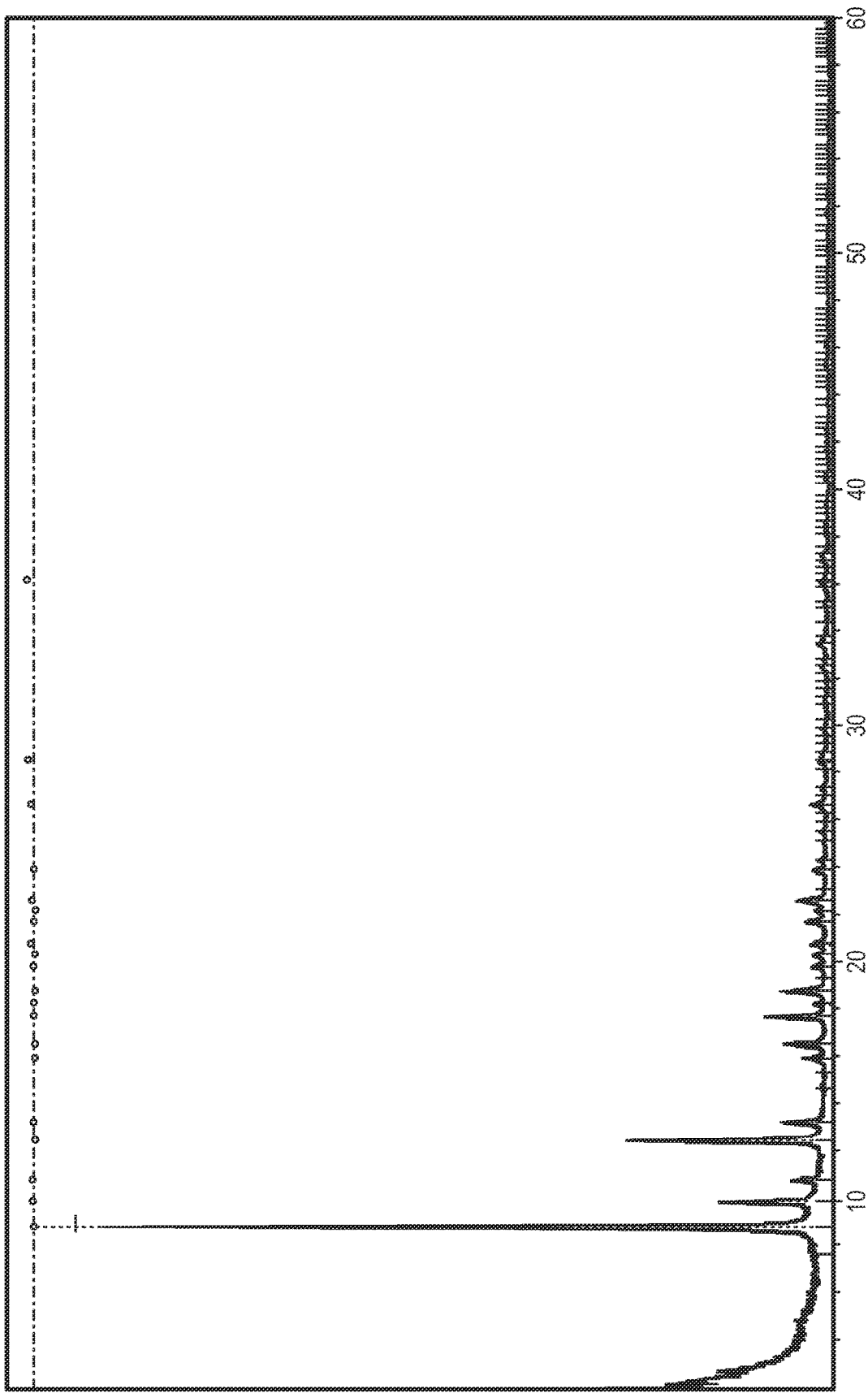
FIG. 7. shows an x-ray powder diffraction pattern of the MOF obtained in Example 1C after completing ammonia addition but before freeze drying.

Example 1C: Mesopore-Containing Metal-Organic Framework Synthesis: 4-pyrazolecarboxylic acid (3.4 g) was dissolved in 800 mL of a 20 vol. % solution of water in ethanol. This solution was heated to 60° C. and 11.4 g $Zn_4O(2,2\text{-dimethylbutanoate})_6$ (2,2-dimethylbutanoate= DMBA) was added as a solid. The reaction began to form solids immediately and was allowed to stir overnight at 70° C. The mixture was then diluted with 480 mL of water. These solids were then filtered and suspended in 200 mL of a 50/50 volume mixture of ethanol and water. A small portion (~0.1 mL) of aqueous ammonia solution was added and mixture stirred for 5 minutes. The solid was analyzed by x-ray diffraction until the powder pattern seen in FIG. 7 is observed. The solid were then isolated by centrifugation and then washed with ethanol followed by cyclohexane. A dry powder was isolated by either letting the cyclohexane-wet solids dry at room temperature, or by freezing the solid in a bath of sufficiently low enough temperature to freeze the suspension of MOF in cyclohexane and then applying a vacuum to remove the cyclohexane via sublimation (freeze drying)

Example 2: Product Characterization. FIG. 1 shows an x-ray powder diffraction pattern for the product obtained in Example 1A collected on a Bruker Endeavor D8 x-ray powder diffractometer. Table 1 lists the 2-theta values (°), d-spacing (Å), and relative intensity H (%) of the x-ray powder diffraction peaks of the product obtained in Example 1A.

TABLE 1

| 2θ (°) | d (Å) | H (%) |
|---|---|---|
| 7.734 | 11.4225 | 9.6 |
| 8.911 | 9.9159 | 100 |
| 9.959 | 8.8747 | 16.9 |
| 10.9 | 8.1103 | 4.2 |
| 12.587 | 7.0267 | 34.9 |
| 13.339 | 6.6323 | 9.2 |
| 16.014 | 5.5302 | 7.6 |
| 16.614 | 5.3316 | 9.5 |
| 17.769 | 4.9874 | 14.1 |
| 18.323 | 4.8379 | 5.4 |
| 18.859 | 4.7018 | 15.5 |
| 19.37 | 4.5787 | 1.9 |
| 19.866 | 4.4656 | 3.9 |
| 20.377 | 4.3548 | 4.7 |
| 20.811 | 4.2649 | 2.9 |
| 21.751 | 4.0826 | 10.1 |
| 22.241 | 3.9939 | 2.8 |
| 22.668 | 3.9195 | 10.5 |
| 23.97 | 3.7094 | 5.5 |
| 24.34 | 3.6539 | 2.9 |
| 25.561 | 3.4821 | 1 |
| 26.733 | 3.332 | 4.9 |
| 27.461 | 3.2453 | 2.4 |
| 28.572 | 3.1216 | 4.7 |
| 28.873 | 3.0897 | 2.7 |
| 29.901 | 2.9858 | 4.2 |
| 30.927 | 2.8891 | 2.3 |
| 31.287 | 2.8567 | 1.8 |
| 32.491 | 2.7535 | 3.6 |
| 33.472 | 2.675 | 3.4 |
| 36.127 | 2.4843 | 3.3 |
| 36.983 | 2.4287 | 3.2 |
| 37.278 | 2.4101 | 2.9 |
| 40.487 | 2.2262 | 1.7 |
| 45.411 | 1.9956 | 2.9 |
| 46.16 | 1.9649 | 1.5 |

Table 2 lists the 2-theta values (°), d-spacing (Å), and relative intensity H (%) of the x-ray powder diffraction peaks of the product obtained in Example 1C (FIG. 7).

TABLE 2

| 2θ (°) | d (Å) | H (%) |
|---|---|---|
| 8.824 | 10.0129 | 10.9 |
| 9.854 | 8.9690 | 38.3 |
| 12.483 | 7.0852 | 100 |
| 13.233 | 6.6852 | 6.6 |
| 14.623 | 6.0527 | 1.3 |
| 15.927 | 5.5600 | 3.5 |
| 16.527 | 5.3595 | 13.8 |

TABLE 2-continued

| 2θ (°) | d (Å) | H (%) |
|---|---|---|
| 17.682 | 5.0119 | 24.1 |
| 18.218 | 4.8655 | 3.1 |
| 18.753 | 4.7281 | 23.2 |
| 19.780 | 4.4849 | 4.1 |
| 20.272 | 4.3771 | 5.1 |
| 20.762 | 4.2749 | 6.0 |
| 21.703 | 4.0916 | 8.7 |
| 22.153 | 4.0095 | 4.8 |
| 23.866 | 3.7254 | 4.5 |

Figure 2:
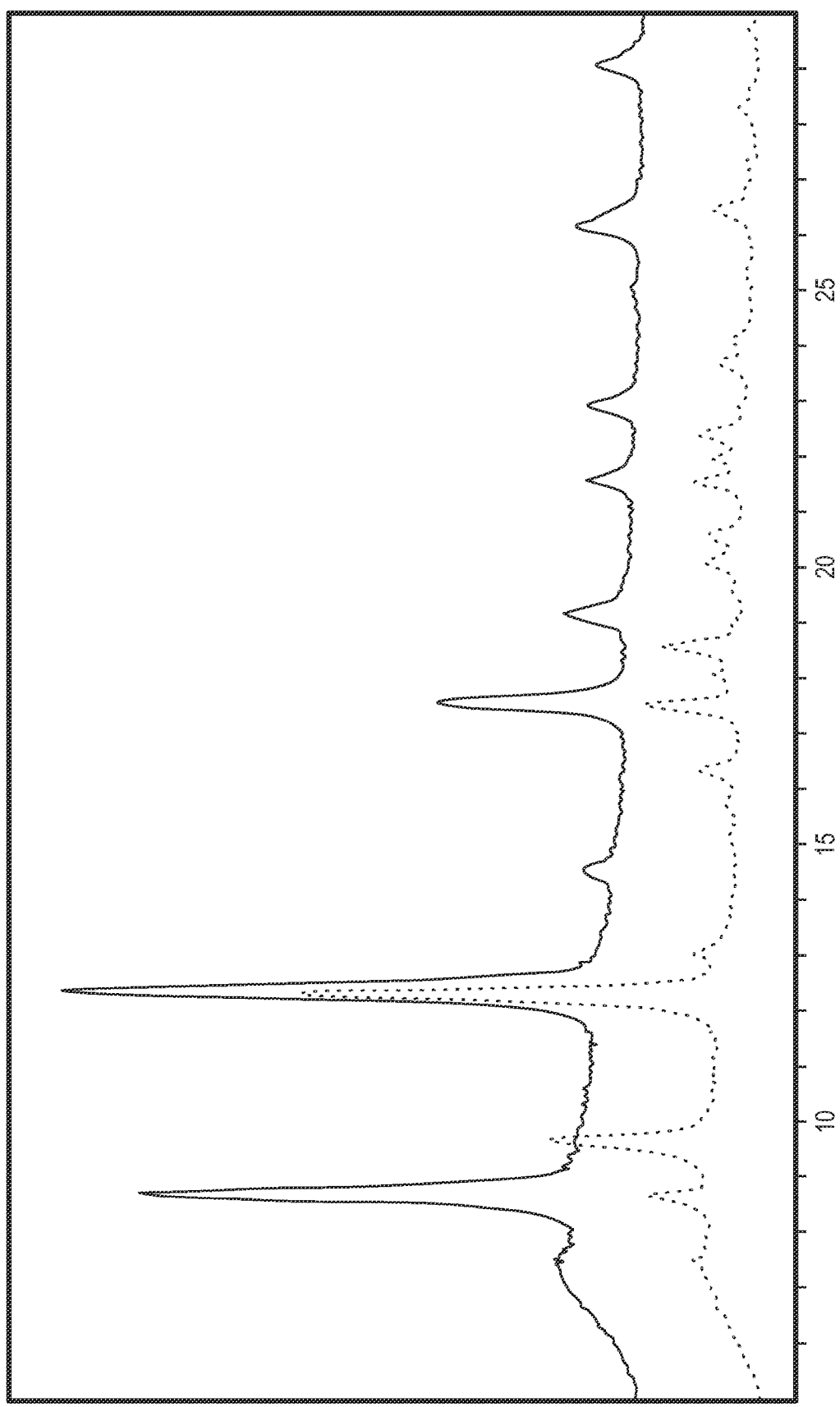
FIG. 2 shows x-ray diffraction patterns for the MOF obtained in Example 1A after exposure to atmospheric water for 3 days (bottom pattern) and after heating to 150° C. under flowing nitrogen for 60 minutes (top pattern).

FIG. 2 shows comparative x-ray powder diffraction patterns of the product obtained in Example 1A after exposure to atmospheric water for 3 days (bottom pattern) and after heating to 150° C. under flowing nitrogen for 60 minutes (top pattern). As shown, the loss of peak density is characteristic of an increase in symmetry. The bottom pattern, with its characteristic Pa3 symmetry, converts to the top pattern with an Fm-3m symmetry after activation under nitrogen.

Figure 3:
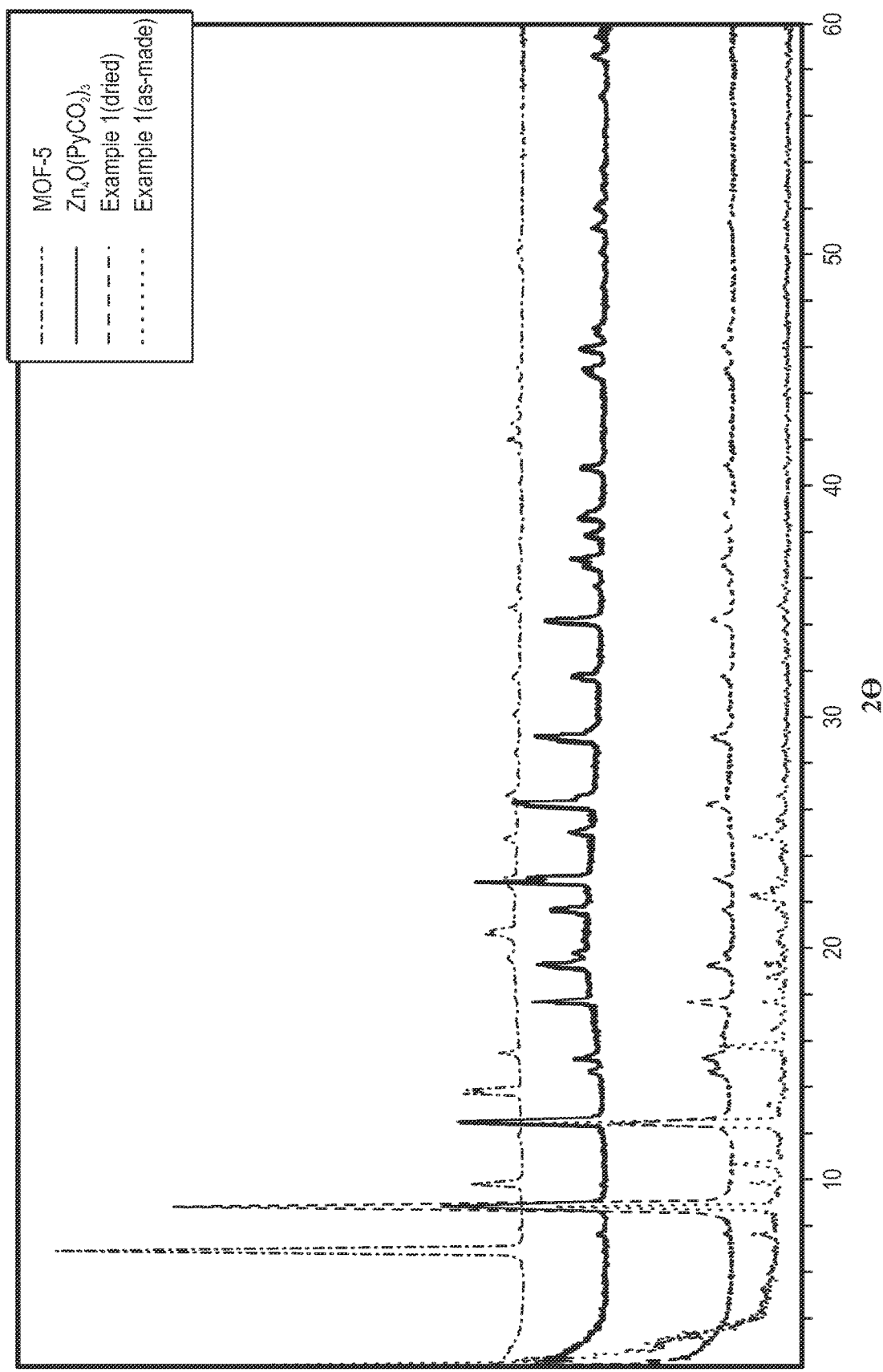
FIG. 3 shows comparative x-ray powder diffraction patterns for the product of Example 1A as-produced and after drying, for MOF-5, and for $Zn_4O(PyCO_2)_3$.

FIG. 3 shows comparative x-ray powder diffraction patterns for the product of Example 1A as-produced and after drying, for MOF-5, and for $Zn_4O(PyCO_2)_3$ (MOF described in Tu et al., J. Am. Chem. Soc., 2014, 136, 14465 as compound 1). The as-synthesized pattern of $Zn_4O(PyCO_2)_3$ of Tu et al. is distinctly different than the product obtained in Example 1A of the present disclosure. Comparing the as-synthesized pattern of $Zn_4O(PyCO_2)_3$ of Tu et al. with the patterns of product obtained in Example 1A (FIGS. 1 and 2) shows that as-synthesized product obtained using a metal carboxylate cluster exhibits Pa3 symmetry, indicated by peaks on either side of the parent peak at 9° 2θ. The pattern of the as-synthesized $Zn_4O(PyCO_2)_3$ of Tu et al. differs from the experimental pattern of the as-synthesized product of Example 1A in that the product obtained in Example 1A exhibits a single peak at about 15° 2θ as well as only 4 peaks below 12° 2θ. This is different from the pattern the as-synthesized $Zn_4O(PyCO_2)_3$ of Tu et al., which has a doublet of peaks at about 15° 2θ with only 2 peaks below 12° 2θ.

Figure 4A:
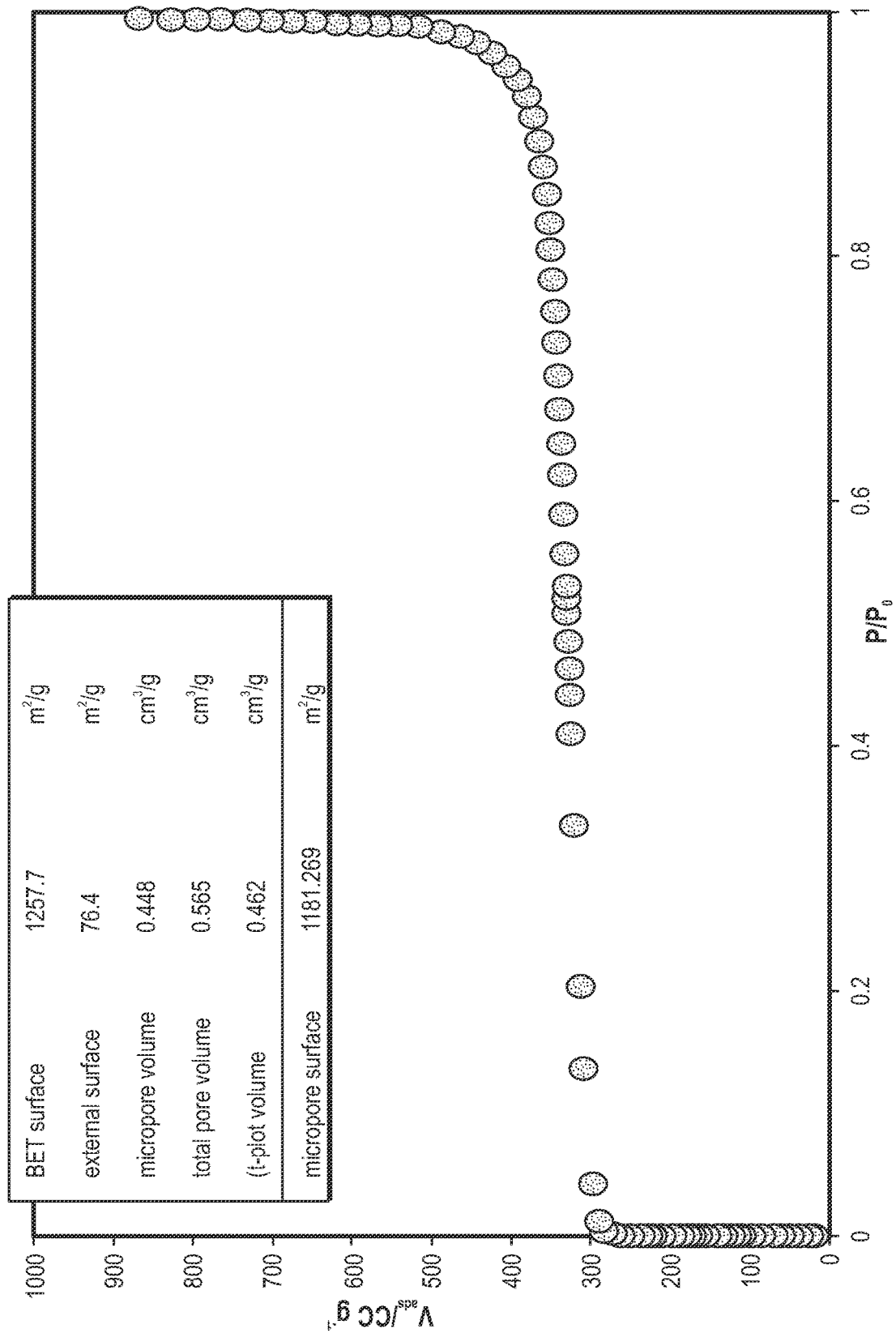
FIGS. 4A and 4B show $N_2$ adsorption isotherms at 77 K for the MOF of Example 1A plotted on $P/P_0$ and Log $P/P_0$ scales, respectively.
Figure 4B:
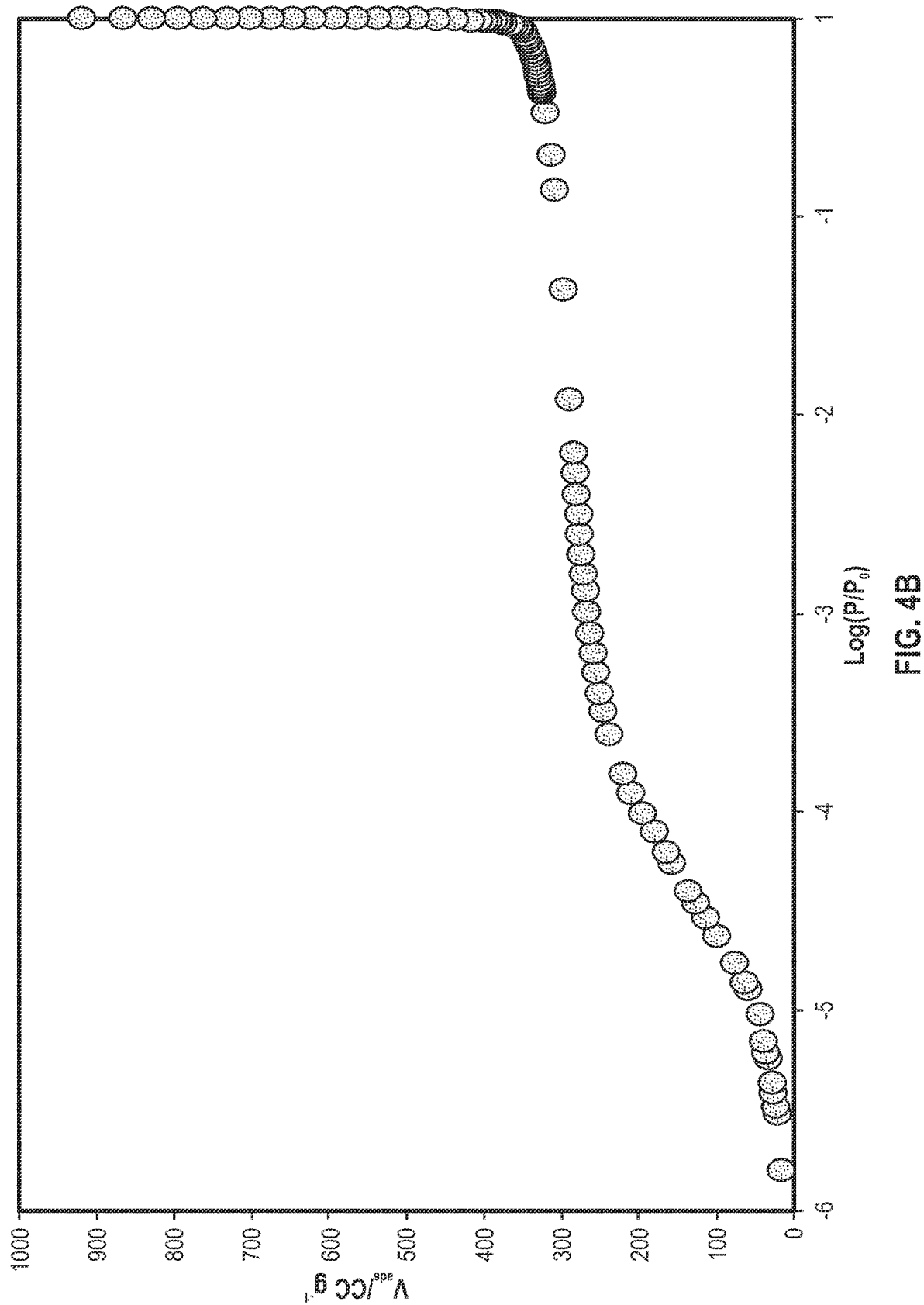

FIGS. 4A and 4B show $N_2$ adsorption isotherms at 77 K for the product of Example 1A plotted on $P/P_0$ and Log $P/P_0$ scales, respectively. The calculated BET surface area was 1257.7 m²/g. The external surface was 76.4 m²/g. The micropore volume was 0.448 cm³/g. The corresponding total pore volume was 0.565 cm³/g. The micropore surface was 1181.269 m²/g.

Figure 5:
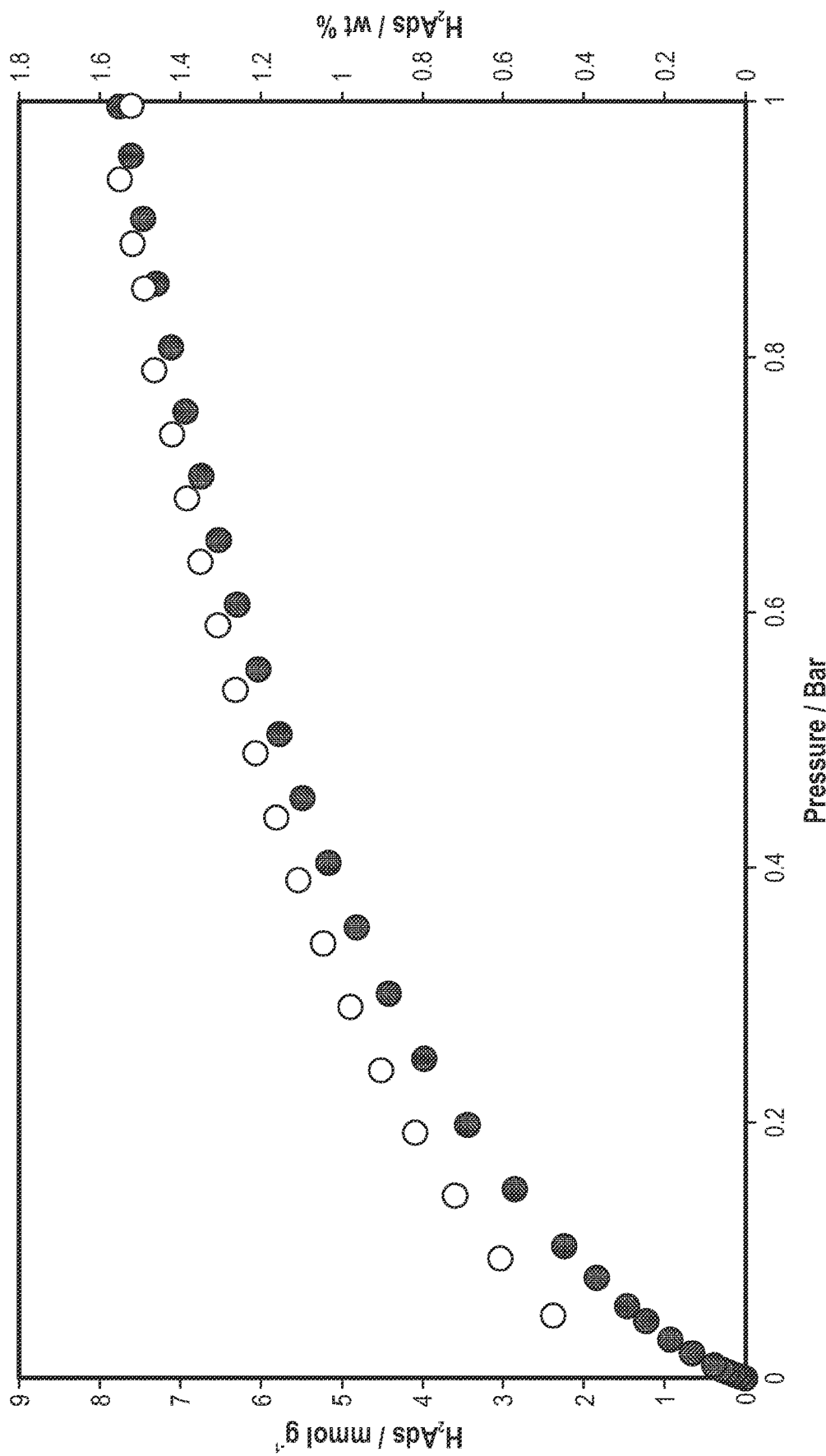
FIG. 5 shows the $H_2$ adsorption/desorption isotherm for the MOF of Example 1A at 7 K.

FIG. 5 shows the $H_2$ adsorption/desorption isotherm for the product of Example 1A at 77 K, with adsorption in mmol/g plotted on the left axis and weight % plotted on the right axis. Adsorption is noted by closed circles and desorption is noted by open circles in FIG. 5. The capacity of this material at 1 bar is comparable to that of MOF-5 on a gravimetric basis and is 75% higher on a volumetric basis.

Figure 6:
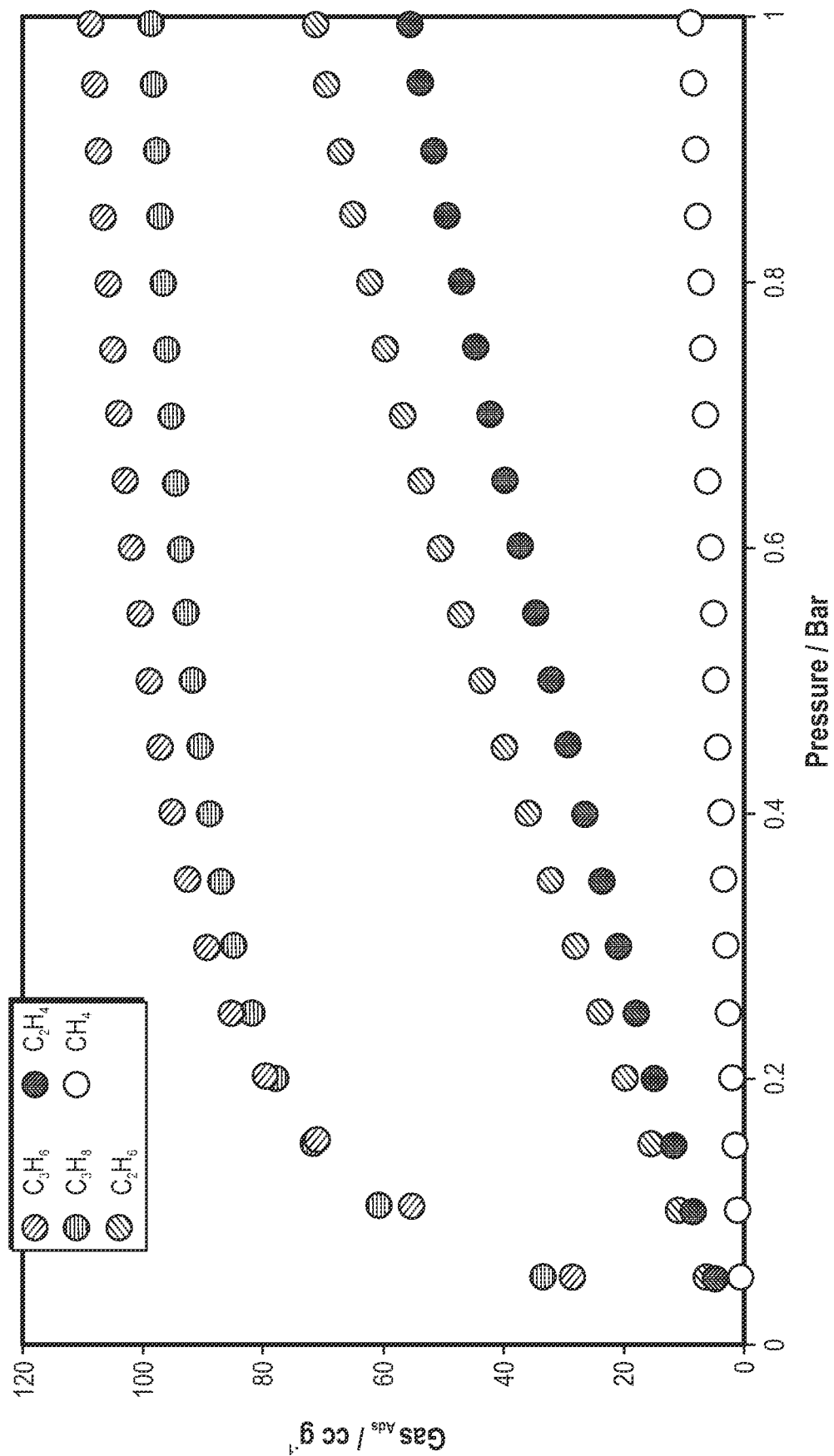
FIG. 6. shows hydrocarbon ($CH_4$, $C_2H_4$, $C_2H_6$, $C_3H_8$, $C_3H_6$) adsorption isotherms for the MOF of Example 1A at 303K.

FIG. 6 shows the hydrocarbon adsorption isotherms for the product of Example 1A at 303 K for various hydrocarbons.

FIG. 7 shows the x-ray powder diffraction pattern of the product of Example 1C after completing ammonia addition but before freeze drying.

Figure 8:
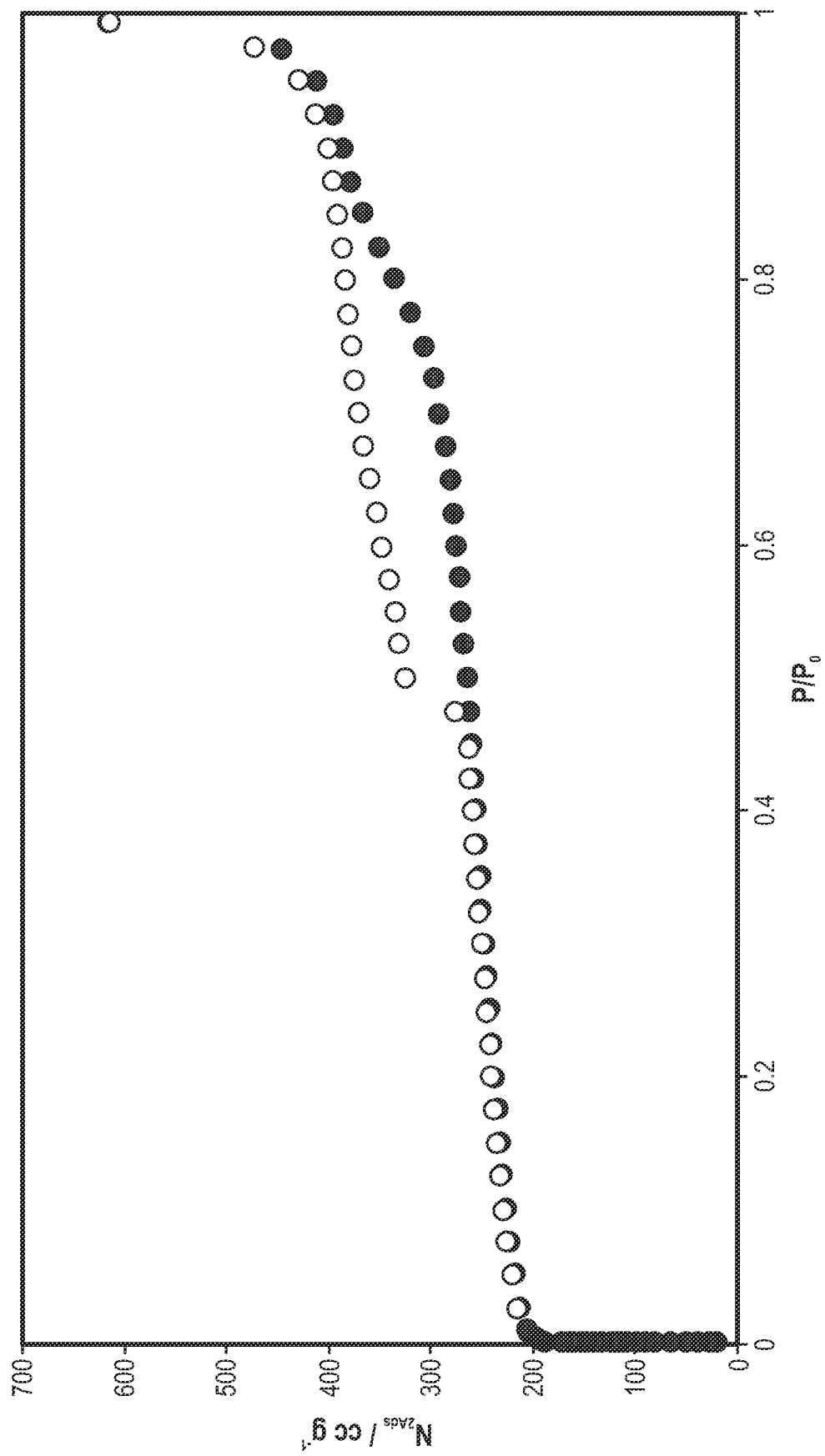
FIG. 8 shows $N_2$ adsorption isotherms at 77 K for the MOF of Example 1C plotted on $P/P_0$ and Log $P/P_0$ scales, respectively.

FIG. 8 shows $N_2$ adsorption isotherms at 77 K for the product of Example 1C plotted on $P/P_0$ and Log $P/P_0$ scales, respectively. The calculated BET surface area was 908 m²/g. The external surface was 189 m²/g. The micropore volume was 0.34 cm³/g. The corresponding total pore volume was 0.64 cm³/g. The micropore surface was 715 m²/g.

Example 3A: Zinc Exchange Using $CoCl_2$. 100 mg of the product of Example 1A was suspended in 10 mL of DMF and between 50 and 200 mg of $CoCl_2$ was added. The solution was then stirred at 60° C. for 18 hours. The solid was isolated by centrifugation and washed with DMF (3×10 mL). The washed solid was then re-suspended in 10 mL of DMF and heated to 60° C. for 4 hours with stirring. This material was then isolated by centrifugation, washed with toluene (3×10 mL), followed by cyclohexane and then allowed to air dry.

Example 3B: Zinc Exchange Using $NiCl_2$. Example 3B was repeated analogously to Example 3A except for using $NiCl_2$ instead of $CoCl_2$.

Example 3C: Zinc Exchange Using $MnCl_2$. Example 3C was repeated analogously to Example 3A except for using $MnCl_2$ instead of $CoCl_2$.

Figure 9:
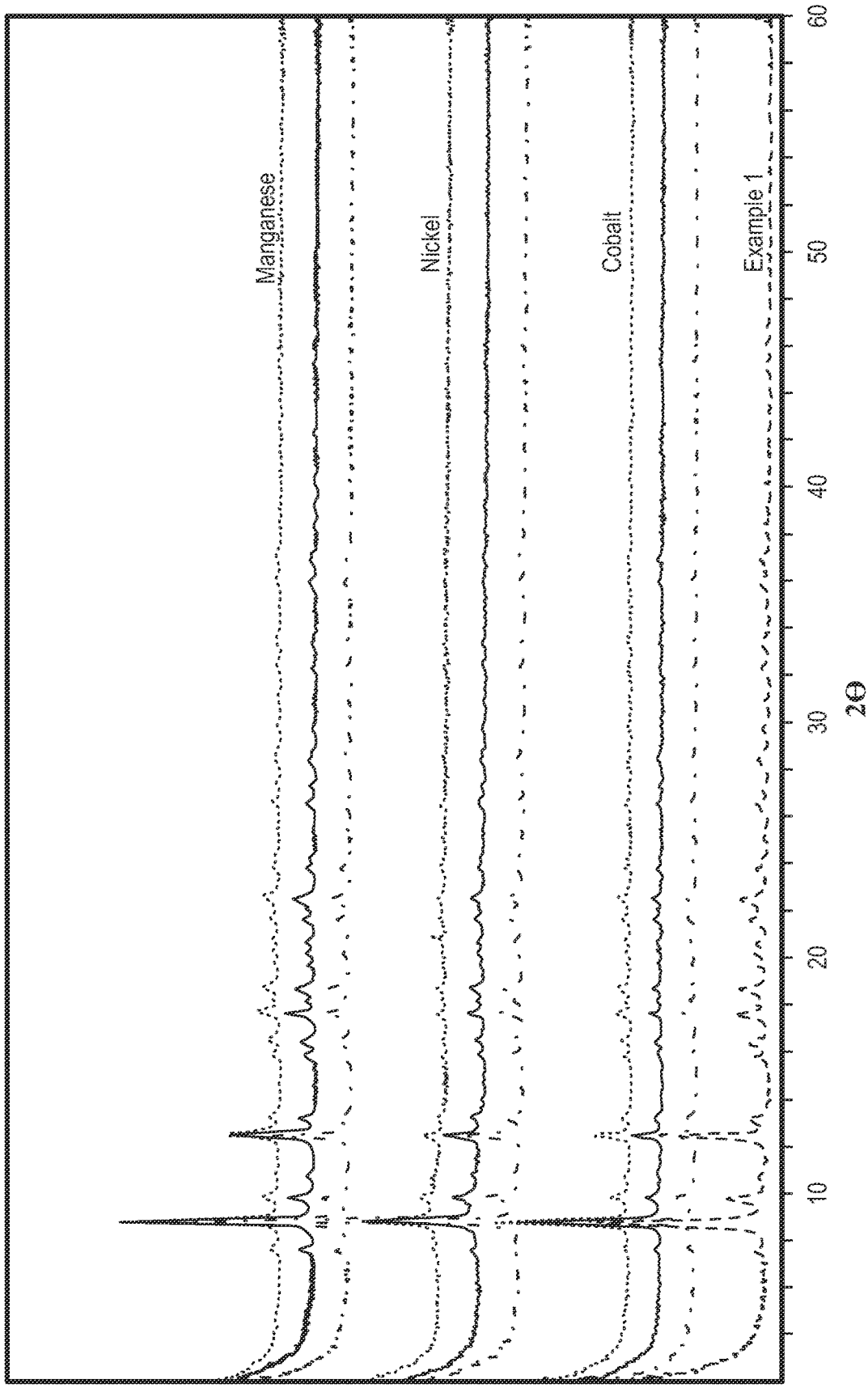
FIG. 9 shows comparative x-ray powder diffraction patterns for the product of Example 1A and the products of Examples 3A, 3B, and 3C.

FIG. 9 shows comparative x-ray powder diffraction patterns for the product of Example 1A and the products of Examples 3A, 3B, and 3C. The three traces of x-ray powder diffraction patterns for each product (Examples 3A, 3B, and 3C) correspond, in ascending order, to the patterns obtained after treatment with 50, 100 and 150 wt. % metal chloride salt. As shown, there was minimal change in the crystallinity and structure of the product following cobalt, nickel, and manganese exchange.

Figure 10A:
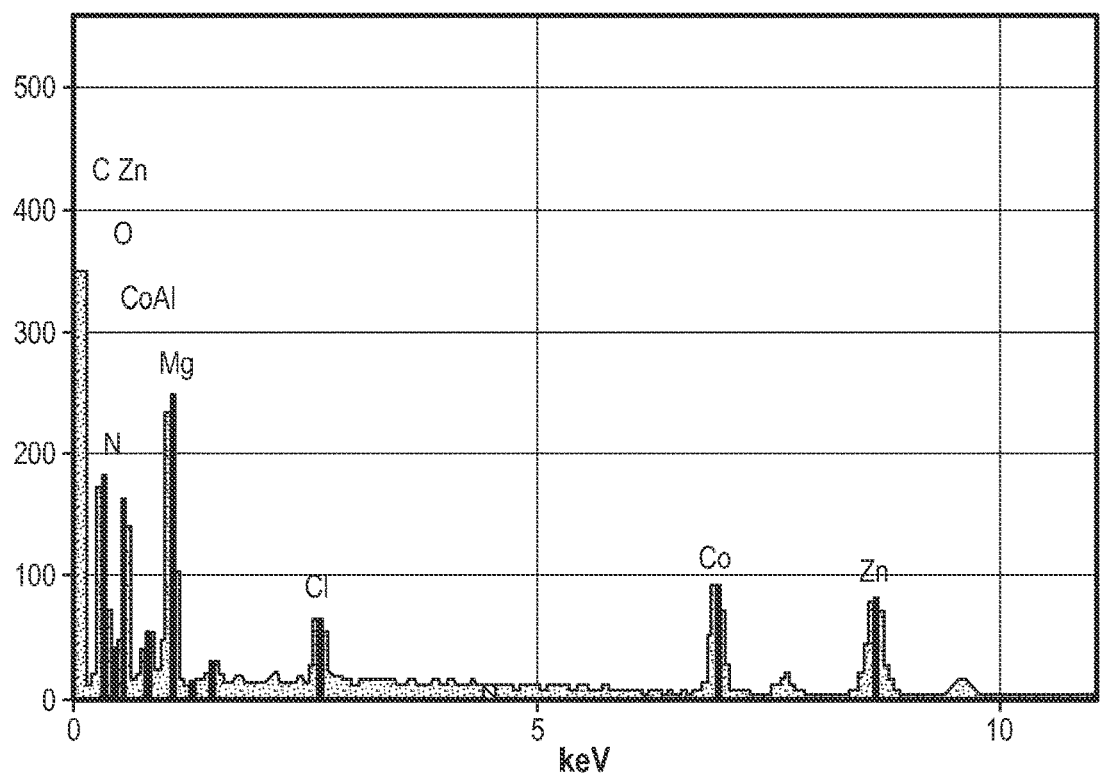
FIG. 10A-10C show energy dispersive x-ray analyses of the products of Examples 3A, 3B, and 3C, respectively.
Figure 10B:
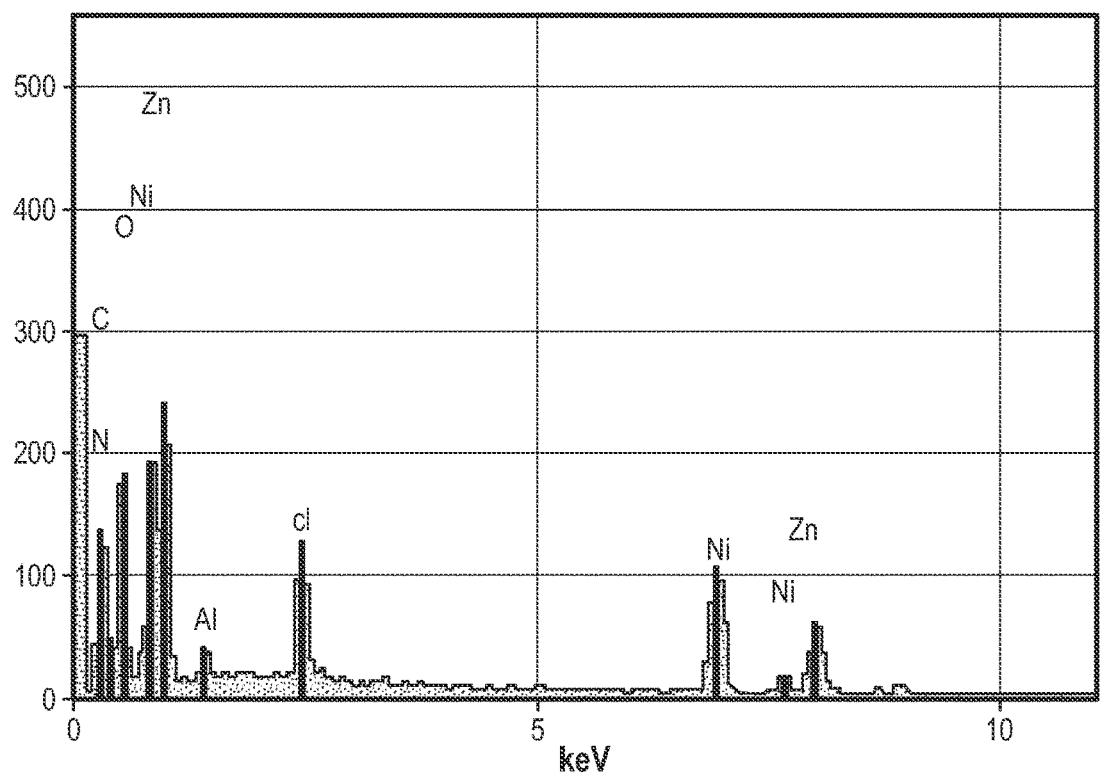
Figure 10C:
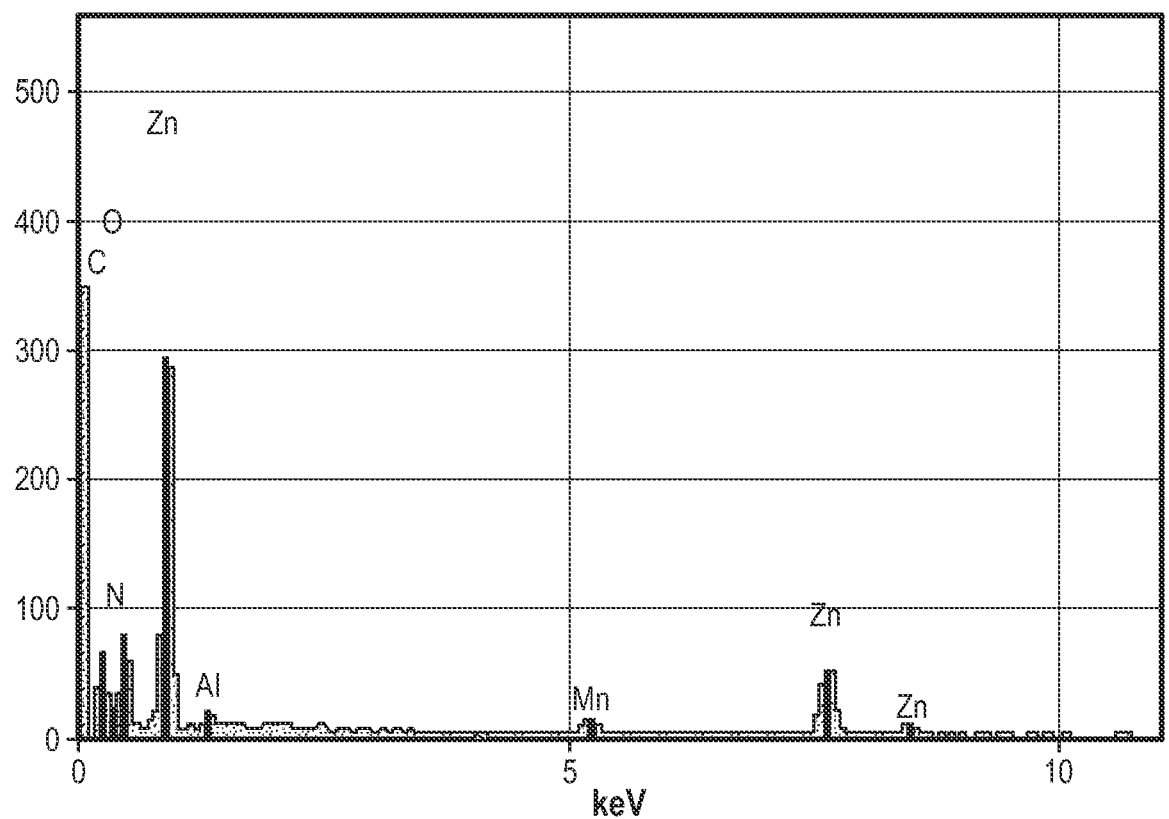

FIG. 10A-10C show energy dispersive x-ray analyses of the products of Examples 3A, 3B, and 3C, respectively.

As shown, the product in FIG. 10A contained both cobalt and zinc, which is indicative of exchange of a portion of the zinc centers for cobalt. Table 3 shows the EDX data for the product of Example 3A.

Based on the observed peak areas the molar ratio of Mn:Zn was approximately 1:3, indicating that some zinc was exchanged by manganese.

Example 4A: Zinc Exchange Using $Co(NO_3)_2$. 100 mg of the product of Example 1 was suspended in 10 mL of DMF and between 50 and 200 mg of $Co(NO_3)_2$ was added. The solution was then stirred at 60° C. for 72 hours. The solid was then isolated by centrifugation and washed with DMF (3×10 mL). The washed solid was then re-suspended in 10 mL of DMF and heated to 60° C. for 4 hours with stirring. This material was then isolated by centrifugation, washed with toluene (3×10 mL), followed by cyclohexane and then allowed to air dry.

Example 4B: Zinc Exchange Using $Ni(NO_3)_2$. Example 4A was repeated analogously except for using $Ni(NO_3)_2$ instead of $Co(NO_3)_2$.

Example 4C: Zinc Exchange Using $Mn(NO_3)_2$. Example 4A was repeated analogously except for using $Mn(NO_3)_2$ instead of $Co(NO_3)_2$.

Nickel-exchanged $Zn_{4-x}Ni_xO(PyCO_2)_3$ after activation at 150° C. under dynamic vacuum showed certain visual differences depending on the nickel source used to promote metal exchange. Samples using $Ni(NO_3)_2$ (Example 4B) and using $NiCl_2$ (Example 3B) for exchange were isostructural but showed visual differences in the chemical environment of the metal centers that was not detectable via x-ray powder

TABLE 3

| Sample ID | C—K | N—K | O—K | Al—K | Cl—K | Co—K | Zn—K |
|---|---|---|---|---|---|---|---|
| Example 3A-1 | 37.84 | 27.39 | 28.00 | 0.47 | 0.54 | 2.05 | 3.71 |
| Example 3A-2 | 37.91 | 24.66 | 28.26 | 0.56 | 0.79 | 2.59 | 5.23 |
| Example 3A-3 | 37.65 | 25.40 | 30.15 | 0.46 | 0.51 | 2.03 | 3.79 |

Based on the observed peak areas, the molar ratio of Co:Zn was approximately 1:1, indicating that some zinc was exchanged by cobalt.

The product in FIG. 10B contained both nickel and zinc, which is indicative of exchange of a portion of the zinc centers for nickel. Table 4 shows the EDX data for the product of Example 3B.

diffraction. The $NiCl_2$ exchanged sample showed a pink color, whereas the $Ni(NO_3)_2$ exchanged sample was off-white following activation. It is speculated that in the product obtained with nickel nitrate, the metal adopts a tetrahedral geometry, resulting in the pink color of the product.

TABLE 4

| Sample ID | C—K | N—K | O—K | Al—K | Cl—K | Ni—K | Zn—K | Br—L |
|---|---|---|---|---|---|---|---|---|
| Example 3B-1 | 42.37 | 23.65 | 28.00 | 0.21 | 1.50 | 2.98 | 1.29 | |
| Example 3B-2 | 45.58 | 24.90 | 24.91 | | 1.09 | 2.39 | 1.12 | |
| Example 3B-3 | 42.49 | 23.77 | 27.03 | | 1.70 | 3.41 | 1.27 | 0.34 |

Based on the observed peak areas, the molar ratio of Ni:Zn was approximately 2:1, indicating that some zinc was exchanged by nickel.

Further, the product in FIG. 10C contained both manganese and zinc, which is indicative of exchange of a portion of the zinc centers for manganese. Table 5 shows the EDX data for the product of Example 3C.

Example 5: Hydrogenation of ethylene using the product of 4B.

Ethylene hydrogenation was used to test for catalytic activity on the product of Example 4B. The product powder was loaded into a vertical, stainless steel tube reactor and heated using a resistively-heated furnace. Ethylene, $H_2$, and inert gas (He) flow rates were controlled using mass flow

TABLE 5

| Sample ID | C—K | N—K | O—K | Al—K | Mn—K | Zn—K |
|---|---|---|---|---|---|---|
| Example 3C-1 | 44.73 | 22.07 | 29.37 | | 0.38 | 3.46 |
| Example 3C-2 | 40.32 | 25.36 | 28.54 | | 0.53 | 5.24 |
| Example 3C-3 | 44.99 | 21.74 | 24.95 | 0.70 | 0.73 | 6.88 | controllers. Concentrations of products were quantified by gas chromatography using an Agilent 7890B instrument and a GasPro column. 15 mg of the MOF of example 4B was loaded into the reactor, and the gas flow rates were set to give 1.7 psi ethylene and 10 psi $H_2$. The temperature of the furnace was increased and the gas composition was analyzed to look for evidence of ethylene hydrogenation. The MOF had negligible hydrogenation activity below 250° C. At 280° C., ethylene conversion to ethane increased rapidly and achieved reached approximately 80% conversion. Ethylene conversion steadily increased beyond 280° C. and finally reached nearly 100% conversion with no signs of deactivation over several hours of activity. No other products (e.g., methane) were detected, suggesting that the MOF is a selective hydrogenation catalyst and does not catalyze undesired hydrogenolysis reactions.

All documents described herein are incorporated by reference herein for purposes of all jurisdictions where such practice is allowed, including any priority documents and/or testing procedures to the extent they are not inconsistent with this text. As is apparent from the foregoing general description and the specific embodiments, while forms of the disclosure have been illustrated and described, various modifications can be made without departing from the spirit and scope of the disclosure. Accordingly, it is not intended that the disclosure be limited thereby. For example, the compositions described herein may be free of any component, or composition not expressly recited or disclosed herein. Any method may lack any step not recited or disclosed herein. Likewise, the term "comprising" is considered synonymous with the term "including." Whenever a method, composition, element or group of elements is preceded with the transitional phrase "comprising," it is understood that we also contemplate the same composition or group of elements with transitional phrases "consisting essentially of," "consisting of," "selected from the group of consisting of," or "is" preceding the recitation of the composition, element, or elements and vice versa.

Unless otherwise indicated, all numbers expressing quantities of ingredients, properties such as molecular weight, reaction conditions, and so forth used in the present specification and associated claims are to be understood as being modified in all instances by the term "about." Accordingly, unless indicated to the contrary, the numerical parameters set forth in the following specification and attached claims are approximations that may vary depending upon the desired properties sought to be obtained by the embodiments of the present invention. At the very least, and not as an attempt to limit the application of the doctrine of equivalents to the scope of the claim, each numerical parameter should at least be construed in light of the number of reported significant digits and by applying ordinary rounding techniques.

Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces.

One or more illustrative embodiments are presented herein. Not all features of a physical implementation are described or shown in this application for the sake of clarity. It is understood that in the development of a physical embodiment of the present disclosure, numerous implementation-specific decisions must be made to achieve the developer's goals, such as compliance with system-related, business-related, government-related and other constraints, which vary by implementation and from time to time. While a developer's efforts might be time-consuming, such efforts would be, nevertheless, a routine undertaking for one of ordinary skill in the art and having benefit of this disclosure.

Therefore, the present disclosure is well adapted to attain the ends and advantages mentioned as well as those that are inherent therein. The particular embodiments disclosed above are illustrative only, as the present disclosure may be modified and practiced in different but equivalent manners apparent to one having ordinary skill in the art and having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope and spirit of the present disclosure. The embodiments illustratively disclosed herein suitably may be practiced in the absence of any element that is not specifically disclosed herein and/or any optional element disclosed herein.

The invention claimed is:

1. A metal-organic framework material comprising:
    a plurality of metal clusters comprising one or more $M_4O$ clusters, wherein M is a metal; and
    a plurality of multidentate organic ligands coordinated to the plurality of metal clusters to define an at least partially crystalline network structure having a plurality of internal pores, the multidentate organic ligand comprising 4-pyrazolecarboxylate;
    wherein the at least partially crystalline network structure has an x-ray powder diffraction pattern comprising characteristic diffraction peaks of at least 7.73, 8.91, 9.96, 10.9 and 12.6 (all ±5%) degree 2-theta (° 2θ).

2. The metal-organic framework material of claim 1, wherein the at least partially crystalline network structure has a cubic topology.

3. The metal-organic framework material of claim 1, wherein the at least partially crystalline network structure has a Pa3 symmetry.

4. The metal-organic framework material of claim 1, wherein at least a portion of the plurality of metal clusters comprise one or more metal centers having a tetrahedral geometry.

5. The metal-organic framework material of claim 1, wherein at least a portion of the plurality of metal clusters comprise a divalent metal.

6. The metal-organic framework material of claim 1, wherein at least a portion of the plurality of metal clusters comprise one or more $M_4O$ clusters and M is zinc, cobalt, nickel, copper, iron, chromium, manganese, or any combination thereof.

7. The metal-organic framework material of claim 1, wherein at least a portion of the plurality of metal clusters comprise one or more $M_4O$ clusters and M is zinc.

8. The metal-organic framework material of claim 1, wherein the at least a portion of the $M_4O$ clusters comprises $Zn_4O$ clusters.

9. The metal-organic framework material of claim 1, wherein the metal-organic framework is a reaction of product of 4-pyrazolecarboxylic acid and a preformed metal clusters comprising $Zn_4O(2,2\text{-dimethylbutanoate})_6$.

10. The metal-organic framework material of claim 1, wherein the internal pores have pore diameters in a range of about 6.0 Å to about 40 Å, the internal pores have a pore volume in a range of about 0.4 cc/g to about 0.64 cc/g, and the at least partially crystalline network structure has a BET surface area in a range of about 750 m$^2$/g to about 1300 m$^2$/g.

11. A method comprising:
   combining a metal source with 4-pyrazolecarboxylic acid, wherein the metal source is a preformed metal cluster; and
   reacting the metal source with the 4-pyrazolecarboxylic acid to form a metal-organic framework material having an at least partially crystalline network structure with a plurality of internal pores defined therein and comprising a plurality of metal clusters coordinated to a 4-pyrazolecarboxylate, the plurality of metal clusters comprising one or more M$_4$O clusters, wherein M is a metal and the at least partially crystalline network structure has an x-ray powder diffraction pattern comprising characteristic diffraction peaks of at least 7.73, 8.91, 9.96, 10.9 and 12.6 (all ±5%) degree 2-theta (° 2θ).

12. The method of claim 11, wherein the preformed metal cluster comprises zinc.

13. The method of claim 11, wherein the preformed metal cluster comprises Zn$_4$O(2,2-dimethylbutanoate)$_6$.

14. The method of claim 11, wherein the metal-organic framework material comprises at least one of a residual ligand, a metal salt or a solvent in at least a portion of the plurality of internal pores.

15. The method of claim 14 further comprising:
   thermally removing the residual ligand, the metal salt, the solvent, or any combination thereof from the plurality of internal pores.

16. The method of claim 15, wherein a symmetry of the metal-organic framework material changes upon removing the residual ligand, the metal salt, the solvent, or any combination thereof.

17. The method of claim 11, wherein the plurality of metal clusters define a plurality of metal centers, the method further comprising:
   exchanging at least a portion of a first metal comprising the plurality of metal centers for a second metal.

18. The method of claim 17, wherein the first metal is zinc and the second metal comprises at least one of cobalt, nickel, or manganese.

19. A method comprising:
   contacting a mixture comprising one or more chemical species with the metal-organic framework material of claim 1.

20. The method of claim 19, wherein the one or more chemical species comprises hydrogen, nitrogen, carbon dioxide, a hydrocarbon, or a mixture thereof.

21. A method comprising:
   providing a catalyst precursor comprising a reaction product of 4-pyrazolecarboxylic acid and a preformed metal cluster, the reaction product being a metal-organic framework material having an at least partially crystalline network structure with a plurality of internal pores defined therein and comprising a plurality of metal clusters comprising a M$_4$O cluster, wherein M is a metal, coordinated to the 4-pyrazolecarboxylate;
   wherein the at least partially crystalline network structure has an x-ray powder diffraction pattern comprising characteristic diffraction peaks of at least 7.73, 8.91, 9.96, 10.9 and 12.6 (all ±5%) degree 2-theta (° 2θ);
   exposing the catalyst precursor to a reducing agent to form an activated catalyst;
   contacting the activated catalyst with an olefin; and
   hydrogenating the olefin while the olefin contacts the activated catalyst.

22. The method of claim 21, wherein at least a portion of the metal clusters comprise zinc, and at least a portion of the zinc is exchanged for a catalytically active metal.

23. The method of claim 22, wherein the catalytically active metal comprises Ni(II).

\* \* \* \* \*